(12) United States Patent
Jia et al.

(10) Patent No.: US 12,371,476 B2
(45) Date of Patent: Jul. 29, 2025

(54) CANINE PARVOVIRUS (CPV) NANOBODY CPV-VHH-H1 AND USE THEREOF

(71) Applicant: Institute of Animal Sciences of Chinese Academy of Agricultural Sciences, Beijing (CN)

(72) Inventors: Hong Jia, Beijing (CN); Hongfei Zhu, Beijing (CN); Weifeng Yuan, Beijing (CN); Shaohua Hou, Beijing (CN); Xiaoyu Guo, Beijing (CN); Yitong Jiang, Beijing (CN); Qianqian Feng, Beijing (CN); Zhaoyang Wang, Beijing (CN); Ting Xin, Beijing (CN)

(73) Assignee: Institute of Animal Sciences of CAAS, Beijing (CN)

( * ) Notice: Subject to any disclaimer, the term of this patent is extended or adjusted under 35 U.S.C. 154(b) by 230 days.

(21) Appl. No.: 17/984,297

(22) Filed: Nov. 10, 2022

(65) Prior Publication Data
US 2023/0192815 A1    Jun. 22, 2023

(30) Foreign Application Priority Data
Nov. 12, 2021 (CN) .......................... 202111337157.X

(51) Int. Cl.
*C07K 16/08* (2006.01)
*C12N 15/86* (2006.01)

(52) U.S. Cl.
CPC ............ *C07K 16/081* (2013.01); *C12N 15/86* (2013.01); *C07K 2317/14* (2013.01); *C07K 2317/569* (2013.01); *C07K 2317/76* (2013.01); *C12N 2750/14323* (2013.01); *C12N 2750/14334* (2013.01); *C12N 2750/14343* (2013.01); *C12N 2750/14352* (2013.01); *C12N 2750/14362* (2013.01)

(58) Field of Classification Search
CPC .............. C07K 16/081; C07K 2317/14; C07K 2317/569; C07K 2317/76; C07K 2317/22; C07K 2317/56; C12N 15/86; C12N 2750/14323; C12N 2750/14334; C12N 2750/14343; C12N 2750/14352; C12N 2750/14362; C12N 7/00; C12N 2750/14134; C12N 5/0686; C12N 15/85; C12N 2510/02; C12N 2800/107; A61K 39/12; A61K 2039/552; A61P 31/20
See application file for complete search history.

(56) References Cited

U.S. PATENT DOCUMENTS

2011/0262348 A1* 10/2011 Movahedi .......... A61K 51/1027
424/1.49

\* cited by examiner

*Primary Examiner* — Daniel E Kolker
*Assistant Examiner* — Dennis Cherian George

(57) ABSTRACT

A heavy-chain variable region sequence of the nanobody CPV-VHH-H1 has the amino acid sequence set forth in SEQ ID NO: 1; and a gene encoding the nanobody CPV-VHH-H1 has the nucleotide sequence set forth in SEQ ID NO: 2. A nanobody immune library of the CPV is constructed by a phage display technology, a specific anti-CPV nanobody CPV-VHH-H1 is obtained by screening, and it is verified by experiments that the nanobody may specifically bind to the CPV. A new nanobody preparation for use in clinical diagnosis and treatment of the CPV can be developed, and a certain theoretical reserve is provided for applying the nanobody to the field of veterinary biological products.

Figure 1A:
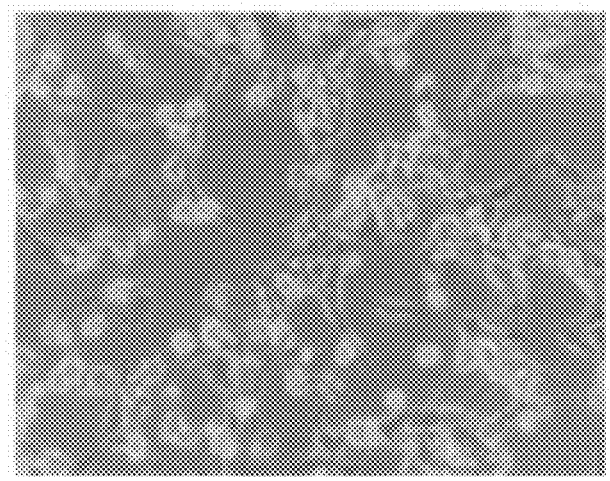
Figure 1B:
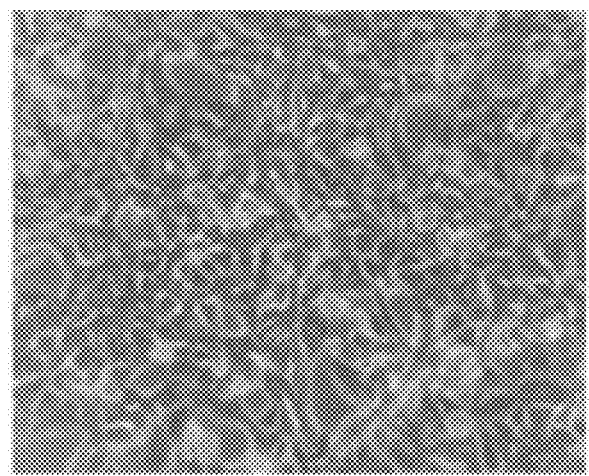

7 Claims, 14 Drawing Sheets
Specification includes a Sequence Listing.

ELISA antibody titers after third/fourth CPV immunizations

FIG.5

FIG. 9

SEQUENCE LISTING

```
Sequence total quantity: 10
SEQ ID NO: 1          moltype = AA   length = 128
FEATURE               Location/Qualifiers
source                1..128
                      mol_type = protein
                      note = Amino acid sequence of the heavy-chain variable
                       region sequence of the nanobody
                      organism = synthetic construct
SEQUENCE: 1
QVQLVESGGG LAQPGGSLRL SCAASGAIDS ISAMRWFRQP PGKQRAVVAS ITSDGVTTYA  60
DSVKGRFTIS RDNAENTLYL QMNSLKTEDT GVYYCYAALK GYSSGVVAAS WGQGTQVTVS  120
GAHHSEDP                                                           128

SEQ ID NO: 2          moltype = DNA  length = 384
FEATURE               Location/Qualifiers
source                1..384
                      mol_type = other DNA
                      note = DNA sequence of the gene encoding the nanobody
                       CPV-VHH-H1
                      organism = synthetic construct
SEQUENCE: 2
caggtgcagc tggtggagtc tggaggaggc ttggcgcagc ctgggggtc tctgagactc    60
tcctgtgccg cctctggagc catcgacagt atctctgcca tgcgctggtt ccgccagcct  120
ccagggaagc agcgcgccgt ggtcgcatcg attacttccg atggtgtcac gacctacgcg  180
gactccgtga agggccgatt caccatctcc agagacaacg ccgagaacac gctgtatctg  240
caaatgaaca gcctgaaaac tgaggacacg ggcgtctatt attgttatgc agccttaaag  300
ggatattcta gtggtgtcgt cgctgcgtcc tggggacagg gacccaggt caccgtctcc    360
ggcgcgcacc acagcgaaga cccc                                         384

SEQ ID NO: 3          moltype = DNA  length = 23
FEATURE               Location/Qualifiers
source                1..23
                      mol_type = other DNA
                      note = Primer VHH F1
                      organism = synthetic construct
SEQUENCE: 3
gtcctggctg ctcttctaca agg                                          23

SEQ ID NO: 4          moltype = DNA  length = 23
FEATURE               Location/Qualifiers
```

```
source                  1..23
                        mol_type = other DNA
                        note = Primer VHH R1
                        organism = synthetic construct
SEQUENCE: 4
ggtacgtgct gttgaactgt tcc                                          23

SEQ ID NO: 5            moltype = DNA  length = 52
FEATURE                 Location/Qualifiers
source                  1..52
                        mol_type = other DNA
                        note = Primer Sfi I-VHH F2
                        organism = synthetic construct
SEQUENCE: 5
gccatgactt ataggcccc aggcggccca gttgcagctc gtggagtcag ga           52

SEQ ID NO: 6            moltype = DNA  length = 57
FEATURE                 Location/Qualifiers
source                  1..57
                        mol_type = other DNA
                        note = Primer Sfi I-VHH R2
                        organism = synthetic construct
SEQUENCE: 6
gccatgactt ataggccg gcctggccgg ggtcttcgct gtggtgcgcc gaggaga       57

SEQ ID NO: 7            moltype = DNA  length = 22
FEATURE                 Location/Qualifiers
source                  1..22
                        mol_type = other DNA
                        note = Primer pComb3x-F
                        organism = synthetic construct
SEQUENCE: 7
aagacagcta tcgcgattgc ag                                           22

SEQ ID NO: 8            moltype = DNA  length = 24
FEATURE                 Location/Qualifiers
source                  1..24
                        mol_type = other DNA
                        note = Primer pComb3x-R
                        organism = synthetic construct
SEQUENCE: 8
gccccttat tagcgtttgc catc                                          24

SEQ ID NO: 9            moltype = DNA  length = 54
FEATURE                 Location/Qualifiers
source                  1..54
                        mol_type = other DNA
                        note = Primer VHH-F
                        organism = synthetic construct
SEQUENCE: 9
ggtggtgtac atctcctaca tctacgcccc cgggcaggtg cagctggtgg agtc        54

SEQ ID NO: 10           moltype = DNA  length = 59
FEATURE                 Location/Qualifiers
source                  1..59
                        mol_type = other DNA
                        note = Primer VHH-R
                        organism = synthetic construct
SEQUENCE: 10
atggtgatgg tggtgctcga gttagtggtg gtggtggtgg tgagaggaga cggtgacct   59
```

CANINE PARVOVIRUS (CPV) NANOBODY CPV-VHH-H1 AND USE THEREOF

CROSS REFERENCE TO RELATED APPLICATION

This patent application claims the benefit and priority of Chinese Patent Application No. 202111337157.X, entitled CANINE PARVOVIRUS (CPV) NANOBODY CPV-VHH-H1 AND USE THEREOF filed on Nov. 12, 2021, the disclosure of which is incorporated by reference herein in its entirety as part of the present application.

REFERENCE TO SEQUENCE LISTING

A computer readable XML file entitled "GWP20220700544 amended sequence listing.xml", that was created on Oct. 16, 2024, with a file size of about 12,344 bytes, contains the sequence listing for this application, has been filed with this application, and is hereby incorporated by reference in its entirety.

TECHNICAL FIELD

The present disclosure relates to the technical field of immunology, in particular to a canine parvovirus (CPV) nanobody CPV-VHH-H1 and use thereof.

BACKGROUND ART

Canine parvovirus (CPV) belongs to the genus Parvovirus, the family Parvoviridae. CPV is a DNA virus that mutates very rapidly, which is almost close to some RNA viruses. The best known of the viruses is canine parvovirus type 2 (CPV-2). In 1978, CPV-2 broke out in the United States and was reported. Since then, CPV has swept the world at an extremely high speed, and CPV-2a, CPV-2b, and CPV-2c mutant strains have appeared one after another. Compared with the original CPV-2, the new mutant strains are more pathogenic and transmissible. Not only are dogs more susceptible to these mutant strains, but also a host range has become wider, even cats can also be infected and get sick. In particular, the CPV-2c mutant strain has stronger virulence, higher pathogenicity, and greater mortality, making prevention and treatment of the CPV more difficult.

Vaccination is currently the most effective means for preventing and controlling the CPV, especially when puppies are vaccinated at the right time. At present, the most used and most effective vaccine is the live attenuated vaccine, which can effectively protect susceptible dogs from CPV infection. Most of strains used in the attenuated vaccines are attenuated CPV-2, and the vaccines exhibit desirable immunogenicity and long duration of immunity. However, with the continuous variation of wild virus strains, the cross-protection reaction between heterologous viruses is weak, and cases of immune failure occur from time to time. Moreover, live vaccines also have biosafety risks such as dispersal and virulence reversion. Therefore, although being currently a vaccine with the highest usage rate and the best immune protection effect, the live attenuated vaccine is not the best choice for the prevention of CPV. With the continuous development of vaccine research technology, the live vaccines may be gradually eliminated.

Nanobodies are antibodies derived from HCAbs, a type of antibody that is found only in camelids and sharks, with the light chains naturally devoid and consisting only of heavy chains. The antigen-binding site of these heavy chain antibodies (HCAbs) is formed by only a single domain structure, namely a Variable domain of Heavy chain of Heavy chain antibody (VHH); and an antibody formed by cloning this structure is the smallest antibody fragment that occurs naturally, such that the antibody is also known as nanobodies (Nabs). Nanobodies are named VHH in camelids. In recent years, there have been increasing studies related to use of nanobodies in the field of animal diseases. For example: Yang Li (2017) et al. constructed an enzyme-linked immunosorbent assay (ELISA) method for quantitative detection of PCV2 using recombinant anti-PCV2 nanobodies as capture antibodies. In this method, the nanobodies effectively reduce the cross-reaction during detection, and provide a better virus content determination method for the production of porcine circovirus vaccine. Yang Yan et al. (2021) constructed a nanobody library against bovine viral diarrhea virus (BVDV) by the phage display technology, and screened a nanobody sequence that reacted well with a BVDV-NS3 protein, laying a solid foundation for prevention and control of BVDV and use and development of nanobodies. At present, no nanobody has been reported for prevention and treatment of the CPV.

SUMMARY

An objective of the present disclosure is to provide a CPV nanobody CPV-VHH-H1 and use thereof, to solve the problems existing in the prior art. In the present disclosure, a nanobody immune library of CPV is constructed by a phage display technology, a specific anti-CPV nanobody CPV-VHH-H1 is obtained by screening, and it is verified by experiments that the nanobody may specifically bind to CPV.

To achieve the above objective, the present disclosure provides the following technical solutions.

The present disclosure provides a CPV nanobody CPV-VHH-H1, where a heavy-chain variable region sequence of the nanobody has the amino acid sequence set forth in SEQ ID NO: 1.

```
SEQ ID NO: 1:
QVQLVESGGGLAQPGGSLRLSCAASGAIDSISAMRWFRQPPGKQRAVVA

SITSDGVTTYADSVKGRFTISRDNAENTLYLQMNSLKTEDTGVYYCYAA

LKGYSSGVVAASWGQGTQVTVSGAHHSEDP
```

The present disclosure further provides a gene encoding the nanobody CPV-VHH-H1, having the nucleotide sequence set forth in SEQ ID NO: 2.

```
SEQ ID NO: 2:
CAGGTGCAGCTGGTGGAGTCTGGAGGAGGCTTGGCGCAGCCTGGGGGGT

CTCTGAGACTCTCCTGTGCCGCCTCTGGAGCCATCGACAGTATCTCTGC

CATGCGCTGGTTCCGCCAGCCTCCAGGGAAGCAGCGCGCCGTGGTCGCA

TCGATTACTTCCGATGGTGTCACGACCTACGCGGACTCCGTGAAGGGCC

GATTCACCATCTCCAGAGACAACGCCGAGAACACGCTGTATCTGCAAAT

GAACAGCCTGAAAACTGAGGACACGGGCGTCTATTATTGTTATGCAGCC

TTAAAGGGATATTCTAGTGGTGTCGTCGCTGCGTCCTGGGGACAGGGGA

CCCAGGTCACCGTCTCCGGCGCGCACCACAGCGAAGACCCC
```

The present disclosure further provides an expression vector including the gene.

In some embodiments, the expression vector is pcDNA3.1.

The present disclosure further provides a host cell including the expression vector.

In some embodiments, the host cell is a HEK293F cell.

The present disclosure further provides use of the nanobody CPV-VHH-H1 in preparation of an anti-CPV drug or vaccine.

The present disclosure further provides an anti-CPV composition including the nanobody CPV-VHH-H1.

The embodiments of the present disclosure have the following technical effects:

In the present disclosure, a nanobody CPV immune library is successfully constructed by the phage display technology, with an initial library capacity of $2\times10^6$ CFU/mL and desirable library diversity. Through three rounds of specific panning, the specific nanobody sequence CPV-VHH-H1 is successfully screened. With a gene recombination technology, a recombinant nanobody CPV-VHH-H1 is successfully expressed through a mammalian cell expression system, and ELISA and IFA identifications each show that the nanobody may specifically bind to the CPV. Therefore, the present disclosure is expected to develop a new nanobody preparation for use in clinical diagnosis and treatment of the CPV, and provides a certain theoretical reserve for applying the nanobody to the field of veterinary biological products.

BRIEF DESCRIPTION OF THE DRAWINGS

To describe the technical solutions in the embodiments of the present disclosure or in the prior art more clearly, the accompanying drawings required for the embodiments are briefly described below. Apparently, the accompanying drawings in the following description show merely some embodiments of the present disclosure, and persons of ordinary skill in the art may still derive other accompanying drawings from these accompanying drawings without creative efforts.

FIGS. 1A-B shows an cytopathic effect (CPE) of CPV-2c on CRFK cells; where FIG. 1A: CPE after the CPV-2c is inoculated to the CRFK cells; FIG. 1B: normal CRFK cells;

FIG. 2 shows a position of CPV particles in a sucrose density gradient;

FIGS. 3A-D shows detection results of a purified virus; where FIG. 3A: CPV after purification; FIG. 3B, FIG. 3C, and FIG. 3D: purified virus after 10-fold, 100-fold and 1000-fold dilution, respectively;

FIG. 4 shows an electron microscope picture of the CPV-2c;

FIG. 5 shows a serum antibody titer detected by ELISA;

FIGS. 6A-C shows results of PCR amplification of a VHH gene; where FIG. 6A: RNA; FIG. 6B: first-round amplification product; FIG. 6C: second-round amplification product (VHH);

FIG. 7 shows an initial colony count of an antibody library;

FIG. 8 shows a PCR result of a bacterial solution; where M is Maker, 1 to 48 are single colony samples;

FIG. 9 shows a phylogenetic tree analysis of a sequence;

FIG. 10 shows a PCR amplification product of the VHH gene;

FIG. 11 shows an enzyme-digested product of the VHH gene;

FIG. 12 shows PCR identification of a recombinant expression vector pcDNA3.1-VHH; where M: 2K DNA Maker; 1 to 12: pcDNA3.1-VHH-H1; 13 to 24: pcDNA3.1-VHH-E3; 25 to 36: pcDNA3.1-VHH-D4; 37 to 48: pcDNA3.1-VHH-F5;

FIG. 13 shows a fluorescence image of a control vector pcDNA3.1-EGFP 24 h after transfection;

FIG. 14 shows a result of SDS-PAGE electrophoresis of a cell culture supernatant;

FIG. 15 shows a result of SDS-PAGE electrophoresis of VHH after purification; and FIGS. 16A-F shows results of an Immunofluorescence Assay (IFA) experiment; where FIG. 16A: VHH CPV-H1; FIG. 16B: VHH CPV-E3; FIG. 16C: VHH CPV-D4; FIG. 16D: VHH CPV-F5; FIG. 16E: secondary antibody control group; FIG. 16F: blank cell control group.

DETAILED DESCRIPTION OF THE EMBODIMENTS

A plurality of exemplary embodiments of the present disclosure is now described in detail. The detailed description should not be considered as a limitation to the present disclosure, but should be understood as a more detailed description of certain aspects, features, and embodiments of the present disclosure.

It should be understood that terms described in the present disclosure are merely used to describe specific embodiments and are not intended to limit the present disclosure. In addition, for a numerical range in the present disclosure, it should be understood that each intermediate value between an upper limit and a lower limit of the range is also specifically disclosed. Each smaller range between any stated values or intermediate value in a stated range and any other stated value or intermediate value in the stated range is also included in the present disclosure. The upper and lower limits of these smaller ranges can independently be included or excluded from the range.

Unless otherwise stated, all technical and scientific terms used herein have the same meaning as commonly understood by those of ordinary skill in the art described in the present disclosure. Although the present disclosure describes only preferred methods and materials, any methods and materials similar or equivalent to those described herein can also be used in the practice or testing of the present disclosure. All documents mentioned in this specification are incorporated by reference to disclose and describe methods and/or materials related to the documents. In case of conflict with any incorporated documents, the content of this specification shall prevail.

It is obvious to a person skilled in the art that a plurality of modifications and variations can be made to the specific embodiments of the present specification without departing from the scope or spirit of the present disclosure. Other embodiments derived from the description of the present disclosure are obvious to a person skilled in the art. The specification and embodiments of the present application are merely exemplary.

As used herein, “including”, “having”, “containing”, and the like are all open terms, which means including but not limited to.

Example 1 Construction and Specificity Screening of CPV Nanobodies

1. Experimental Materials 1.1 Virus Species, Cells, Vectors and Experimental Animals CPV-2c (TS02 strain F12 generation) was provided by Institute of Animal Sciences of Chinese Academy of Agricultural Sciences; cat kidney cells (CRFK, F86 generation) were provided by Institute of Animal Sciences of Chinese Academy of Agricultural Sciences; healthy alpacas (24-month-old, male) and a pComb3x vector were purchased from Abiocenter (Jiangsu) Biotechnology Co., Ltd.; TG1 competent cells were purchased from Beijing Biomed Gene Technology Co., Ltd.; and DH5a was purchased from Nanjing Vazyme Company.

1.2 Preparation of Main Reagent Solutions

1) Luria-Bertani (LB) liquid medium: 10 g of tryptone, 5 g of a yeast extract, and 10 g of sodium chloride were added to 800 mL of deionized water, stirred until completely dissolved, and then diluted to 1 L; an obtained solution was autoclaved after packaging, and stored at room temperature for future use.

2) LB solid medium (ampicillin+(Amp+)): 10 g of tryptone, 5 g of a yeast extract, 10 g of sodium chloride, and 15 g of an agar powder were added to about 800 mL of deionized water, heated and stirred until completely dissolved, air-dried to room temperature, and diluted to 1 L; an obtained solution was autoclaved at 121° C. for 20 min, cooled to about 50° C., and added with 1 mL of an ampicillin solution; a well-mixed solution was dispensed into a disposable sterile petri dish, allowed to stand for solidification, and then stored at 2° C. to 8° C. for later use.

3) Ampicillin solution (100 mg/mL Amp): 5 g of ampicillin was completely dissolved in about 40 mL of deionized water, and diluted to 50 mL; a resulting solution was sterilized by filtration with a 0.22 μml syringe filter, dispensed into 1.5 mL EP tubes, and stored at −20° C.

4) pH 8.0 20 mM Tris-HCl buffer: 2.42 g of a Tris powder was dissolved in about 900 mL of deionized water by stirring, with the pH value adjusted to 8.0 using an appropriate amount of hydrochloric acid, and a resulting solution was diluted to 1 L at room temperature, sterilized with 0.22 μm filtration, and stored at room temperature for later use.

5) Coating buffer (pH 9.6 50 mM carbonate buffer): 1.59 g of sodium carbonate and 2.93 g of sodium bicarbonate were dissolved in about 800 mL of deionized water with stirring, with the pH value adjusted to 9.6, and a resulting solution was diluted to 1 L.

6) 10× phosphate buffered saline (PBS) buffer: 2 g of potassium dihydrogen phosphate, 29 g of disodium hydrogen phosphate dodecahydrate, 2 g of potassium chloride, and 80 g of sodium chloride were added to about 800 mL of deionized water, adjusted the pH value to 7.4, and diluted to 1 L.

7) Washing buffer (PBST): 100 mL of the 10×PBS buffer and 0.5 mL of Tween-20 were diluted to 1 L with deionized water.

8) 20%/30%/40%/50% sucrose solution: 6 g/9 g/12 g/15 g of sucrose were completely dissolved in about 20 mL of a 20 mM Tris-HCl buffer separately, and diluted to 30 g using a buffer, and sterilized by filtration at 0.45 μm.

9) SOC medium: 20 g of tryptone, 5 g of a yeast extract, and 0.5 g of sodium chloride were added in about 900 mL of deionized water, added with 10 mL of 250 mM potassium chloride, stirred until completely dissolved, diluted to 1 L, autoclaved, and stored at room temperature for later use. Before use, 5 mL of sterile 2M magnesium chloride and 9 mL of sterile 40% dextrose solution were added.

2. Experimental Methods 2.1 Propagation and Purification of CPV 1 cluster of CRFK cryopreserved cell were revived in a DMEM medium containing 5% FBS, and incubated in a 37° C., 5% $CO_2$ incubator; the cells were passaged every 2 d to 3 d, and expanded after the cells were stable. During passage, the cells were simultaneously inoculated with the virus strain CPV-2c TS02 at a ratio of 1%, incubated at 37° C., 5% $CO_2$ for 4 d to 5 d, and harvested when about an 80% cytopathic effect (CPE) was reached; the harvested cells were frozen and thawed at −20° C. 3 times, centrifuged at 8,000 rpm for 5 min, and a supernatant was collected. The cell culture supernatant was concentrated 10-fold with an ultrafiltration membrane pack with a molecular weight cut-off of 10 kD, placed on a 20% sucrose pad, and ultracentrifuged at 30,000 rpm for 3 h, and obtained pellets were resuspended with an appropriate amount of a 20 mM Tris-HCl buffer. The obtained resuspended virus was placed on an upper layer of each sucrose solution in a density gradient of 20%, 30%, 40%, and 50%, and after centrifugation at 35,000 rpm for 3 h, a virus band located in an area of 30% to 40% sucrose density was aspirated using a syringe; after diluted with an appropriate amount of buffer, the virus was precipitated again by ultracentrifugation to remove the sucrose in a suspension, and pellets were resuspended with an appropriate amount of the buffer. A purified virus suspension was identified by CPV antigen detection test strips and transmission electron microscopy, and the protein concentration was determined by UV spectrophotometer for subsequent reference.

2.2 Obtaining Highly Immune Peripheral Blood 2.2.1 Vaccine Preparation and Immunization The purified virus was mixed with an equal volume of Freund's complete adjuvant/Freund's incomplete adjuvant at a final concentration of 300 μg/ml for emulsification. A 24-month-old healthy male alpaca was immunized with a vaccine prepared in Freund's complete adjuvant for primary immunization by multiple intramuscular injections (4 points on both sides of the spine and 4 points in the armpit, each inoculated with 0.2 mL). Multiple booster immunizations were conducted on the 14th, 28th and 42nd days after the primary immunization, respectively. The booster immunization was conducted with the vaccine prepared by the incomplete Freund's adjuvant, and the immunization method and dosage were the same as the primary immunization.

2.2.2 Antibody Level Monitoring

The peripheral blood of the immunized alpaca was collected on the 14th day after the third and fourth immunizations separately, a serum was separated, and a CPV antibody titer was detected by ELISA. The ELISA detection method included:

(1) Plate coating: the purified CPV was diluted to 5 μg/mL with the coating buffer, added into a 96-well ELISA plate at 100 μL/well, and placed at 4° C. overnight, the coating buffer was discarded, and the CPV was washed 5 times with PBST.

(2) Blocking: 300 μL of PBSM (PBS containing a 5% nonfat milk powder) was added to each well for blocking at 37° C. for 2 h; a blocking solution was discarded, and the CPV was washed 5 times with PBST, spin-dried and stored at −20° C. for later use.

(3) Dilution and incubation of a serum to be tested: a alpaca serum collected 14 days after the third and fourth immunizations was diluted to 1,000 times, 5,000 times, 25,000 times and 125,000 times, and add to coated ELISA plates at 100 μL/well, and 2 wells for each dilution; meanwhile, a alpaca serum that was not immunized with CPV was used as a negative control; the sera were discarded after incubation at 37° C. for 1 h, and the plates were washed 5 times with PBST.

(4) Secondary antibody incubation: 100 μL of a 10,000-fold diluted Goat Anti-Alpaca IgG H&L (HRP) secondary antibody was added to each well, and incubated at 37° C. for 1 h, the secondary antibody was discarded, and the plates were wash 5 times with PBST.

(5) Color development: 100 µL of a TMB color development solution was added to each well for incubation in the dark for 15 min.

(6) Termination: 50 µL of a 2 M sulfuric acid solution was added to terminate the color development.

(7) Determination of results: an $OD_{450}$ value was measured, a ratio of average absorbance values of sample serum to negative serum >2.1 was determined as positive, and a maximum dilution factor of absorbance value reaching a positive standard was regarded as an antibody titer of the serum.

2.2.3 VHH Gene Amplification 2.2.3.1 Isolation of Lymphocytes

On the 14th day after the fourth immunization, about 30 mL of alpaca peripheral blood was collected through the jugular vein, and divided into anticoagulation tubes, and the anticoagulation tubes were slowly inverted several times to prevent blood coagulation. The lymphocytes were separated within 2 h according to instructions of a lymphocyte separation medium. The collected fresh blood was diluted with normal saline at a ratio of 1:1; 5 mL of a lymphocyte separation solution was added into a 10 mL horizontal centrifuge tube, 5 mL of diluted blood was slowly added above the lymphocyte separation medium, and centrifuged horizontally at 1,500 rpm for 20 min; the white cloudy lymphocytes in the middle layer were carefully aspirated with a syringe. After diluted by 5 times with the normal saline, the aspirated lymphocytes were carefully added above a same amount of the lymphocyte separation solution, and centrifuged horizontally at 1,500 rpm for 20 min; after repetition of the above step once, the lymphocytes washed out in the last wash were diluted and centrifuged at 1,000 rpm for 10 min, and obtained pellets were resuspended with an appropriate amount of the normal saline. The isolated lymphocytes was extracted to obtain RNA as soon as possible, or frozen at −70° C. with an appropriate amount of Trizol.

2.2.3.2 RNA Extraction

RNA was extracted by a Trizol method, including the following steps:

(1) 100 µL of a separated lymphocyte suspension was placed in a centrifuge tube, added with 1 mL of Trizol, and a resulting mixture was repeatedly pipetted and mixed, and then stored at room temperature for 5 min to 10 min.

(2) 0.2 mL of chloroform was added, and the mixture was shaken vigorously for 15 sec, and allowed to stand at room temperature for 5 min.

(3) After the mixture was centrifuged at 12,000 rpm for 15 min, obvious layers were observed, and an upper aqueous phase was aspirated into a new centrifuge tube.

(4) An equal volume of pre-cooled isopropanol was added, and mixed well, and a resulting mixture was allowed to stand for 10 min at room temperature.

(5) Centrifugation was conducted at 12,000 rpm for 15 min, a supernatant was discarded, and pellets were washed with 1 mL of RNase-free 75% ethanol.

(6) Centrifugation was conducted at 8,000 rpm for 10 min, a supernatant was discarded, and obtained pellets were air-dried at room temperature for 5 min to 10 min.

(7) The pellets were resuspended with 50 µL of DEPC water by pipetting appropriately, and the dissolution was accelerated in a water bath at 56° C. for 5 min. A small amount of RNA solution was collected to measure the OD value and subjected to gel electrophoresis, and the rest was stored at −80° C.

2.2.3.3 Reverse Transcription

The RNA of qualified quality was reverse-transcribed according to instructions of a Takara's cDNA synthesis kit. Specific operations were as follows:

1) The following reaction mixtures were prepared in PCR tubes, as shown in Table 1.

TABLE 1

| Reverse transcription system 1 | |
| --- | --- |
| Reagent | Volume (µL) |
| Oligo dT Primer | 1 |
| Random$^6$mers | 1 |
| dNTP Mixture (10 mM each) | 1 |
| Total RNA | 5 |

2) After 5 min of reaction at 65° C., a product was quickly cooled in an ice powder for 2 min.

3) The following components were added to the above reaction solution, as shown in Table 2.

TABLE 2

| RNA reverse transcription system 2 | |
| --- | --- |
| Reagent | Volume (µL) |
| Above reaction solution | 10 |
| 5 × PrimeScript II Buffer | 4 |
| RNase Inhibitor (40 U/µl) | 0.5 |
| PrimeScript II RTase (200 U/µl) | 1 |
| RNase Free dH$_2$O | 4.5 |

4) All the above reaction solutions were placed at 30° C. for 10 min, reacted at 42° C. for 50 min, then at 95° C. for 5 min, and stored at −20° C. for later use.

2.2.3.4 PCR Amplification of VHH Gene

PCR primers for two rounds of nest were designed according to a method of Yang Yanli et al. (Yang Yanli et al., 2019) to remove interference of a VH gene in alpaca; meanwhile, a Sfi I restriction site was introduced into the second round of PCR primers, and primer sequences were as follows:

```
first round of PCR primers:
VHH F1:
                                      (SEQ ID NO: 3)
5'-GTCCTGGCTGCTCTTCTACAAGG-3';

VHH R1:
                                      (SEQ ID NO: 4)
5'-GGTACGTGCTGTTGAACTGTTCC-3';

second round of PCR primers:
Sfi I-VHH F2:
5'-GCCATGACTTATATAGGCCCAGGCGGCCCAGTTGCAGCTCGTGGAG TCAGGA-3' (SEQ ID NO: 5, underlined part was the
Sfi I restriction site);

Sfi I-VHH R2:
5'-GCCATGACTTATATAGGCCGGCCTGGCCGGGGTCTTCGCTGTGGTG

CGCCGAGGAGA-3' (SEQ ID NO: 6, underlined part was
the Sfi I restriction site);
```

With the reverse transcribed cDNA in 2.2.3.3 as a template, a VHH gene fragment was amplified using the first round of PCR primers. The PCR reaction system is shown in Table 2-5, and the amplification procedure is shown in Table 4. A PCR product was identified by 1.0% nucleic acid gel electrophoresis, and it was confirmed that a target band with a size of about 400 bp was successfully amplified; the second round of amplification was conducted using the second round of PCR amplification primers, with the target band as a template. An amplification system and a procedure were the same as those in the first round, as shown in Table 3 and Table 4. A final amplification product was identified by gel electrophoresis and a target fragment was recovered by gel.

TABLE 3

PCR amplification system

| Reagent/sample | Volume (μL) |
| --- | --- |
| Template | 5 |
| Upstream primer | 2 |
| Downstream primer | 2 |
| 2 × Phanta Max MasterMix | 25 |
| ddH$_2$O | 16 |
| Total Volume | 50 |

TABLE 4

PCR amplification program

| Process | Reaction temperature (° C.) | Reaction time |
| --- | --- | --- |
| Pre-denaturation | 95° C. | 5 min |
| Denaturation | 95° C. | 10 s |
| Annealing | 56° C. | 15 s |
| Extension | 72° C. | 30 s |
| Re-extension | 72° C. | 10 min |
| Storage | 4° C. | ∞ |

2.2.4 Construction of an M13 Phage Antibody Library 2.2.4.1 Vector Construction

The target fragment recovered by the second round of PCR in 2.2.3.4 and a pComb3× vector were digested with a Sfi I enzyme separately. The enzyme digestion reaction system is shown in Table 5. The components were added to PCR tubes, mixed and centrifuged briefly to the bottom of the tube, and reacted at 37° C. overnight.

TABLE 5

Enzyme digestion reaction system

| Reaction Component | Volume |
| --- | --- |
| SfiI | 1 μL |
| 10 × CutSmart Buffer | 5 μL |
| Target fragment/vector | 1 μg |
| ddH$_2$O | Up to 50 μL |
| Total Volume | 50 μL |

The target fragment was recovered after the digestion product was identified by nucleic acid electrophoresis gel. A ligation system was adjusted according to a concentration of recovered nucleic acid, and the VHH gene fragment was ligated with the pComb3× vector by a T4 DNA ligase. The ligation reaction system is shown in Table 6, and the reaction was conducted at 37° C. for 30 min.

TABLE 6

T4 DNA ligase ligation system

| Reaction Component | Volume |
| --- | --- |
| T4 DNA Ligase | 1 μL |
| 10 × T4 DNA Ligase Buffer | 1 μL |
| Target fragment and vector recovered after enzyme digestion | Fragment and vector have a molar ratio of approximately 1:3 |
| ddH$_2$O | Up to 10 μL |
| Total Volume | 10 μL |

2.2.4.2 Electric Conversion

A ligation product was introduced into TG1 competent cells by electroporation, and the specific electroporation steps included the followings:

(1) 1 cluster of TG1 electrotransformed competent cells was thawed on ice, and after the competent cells were completely thawed, 10 μL of the ligation product was added, and then allowed to stand on ice for 10 min, where all operations were conducted on ice as much as possible;

(2) the above competent cells were gently transferred into a pre-cooled electroporation cup, and electroshock was conducted once at 1,800 V; a product was added with 1 mL of a SOC medium immediately, and gently transferred to a 2 mL EP tube;

(3) the cells were incubated at 37° C. and 200 rpm by shaking for 1 h, and all cells were spread on an LB (Amp+) solid plate, and incubated overnight at 37° C. upside down; and (4) all colonies grown on the plate were collected into 5 mL of an LB medium, and then added to 5 mL of an LB medium containing 40% glycerol, to obtain an initial antibody library of the anti-CPV nanobodies; the antibody library was aliquoted and stored at −80° C.

2.2.4.3 Identification of the Initial Antibody Library

1) Determination of library capacity: 10 μL of a bacterial solution of the initial antibody library was diluted 1,000 times with the LB medium, and 200 μL of a diluted bacterial solution was spread on a solid LB (Amp+) medium plate, and incubated at 37° C. overnight upside down. The number of colonies on the plate was counted the next day, and a capacity of the initial library was calculated according to the following formula. The screening needs was met when a library capacity reached $10^5$ to $10^6$. All volumes were calculated in μL.

Library capacity (CFU/mL)=(colony number/coated bacterial solution volume)×dilution factor×(1000/original library sampling volume)

2) Detection of positive rate: 48 single colonies were randomly selected from the above plate, added with 500 μL of the LB (Amp+) medium, and incubated with shaking at 37° C. and 200 rpm for 4 h; with an obtained product as a template, PCR amplification was conducted with the amplification primers Sfi I-VHH F2 and SfiI-VHH R2 of the VHH gene, and the amplification system and conditions were the same as those in Table 2-5 and Table 2-6. PCR products were detected by 1.5% gel electrophoresis and the positive rate was calculated.

3) Antibody library diversity analysis: 20 bacterial solutions that were positive in the above PCR test were selected randomly and sent to a sequencing company for sequencing; sequencing results were analyzed with DNAMAN and MEGA software, and a phylogenetic tree was plotted to analyze the antibody library diversity.

2.2.5 Panning and Enrichment of CPV-Specific Recombinant Phages 2.2.5.1 Amplification and Rescue of VHH Antibody Library 1) 100 μL of an initial library bacterial solution was added to 100 mL of the LB (Amp+) medium, and incubated by shaking at 37° C. for 4 h to 6 h, such that an $OD_{600}$ value of the bacterial solution reached 0.6 to 0.8.

2) A helper phage M13K07 was added, an addition amount was calculated according to a multiplicity of infection (MOI) of 20:1; after allowed to stand at 37° C. for 30 min, the bacterial solution was incubated at 37° C. and 180 rpm with shaking for 30 min.

3) The above bacterial solution was centrifuged at 5,000 rpm for 10 min at room temperature, and a supernatant was discarded.

4) The bacterial solution was resuspended with 200 mL of an LB (Amp+, Kana+) medium, and incubated at 30° C. and 200 rpm with shaking overnight.

5) The above culture solution was centrifuged at 4° C. and 8,000 rpm for 20 min, a supernatant was collected into a clean and sterile glass Erlenmeyer flask, slowly added with ⅕ volume of a 5×PEG/NaCl solution, and allowed to stand at 4° C. for 5 h.

6) An obtained solution was centrifuged at 4° C. and 8,000 rpm for 30 min, and a supernatant was discarded fully; obtained pellets were resuspended with 2 mL of PBS, mixed well, and centrifuged at 8,000 rpm for 2 min, and the pellets were discarded; an obtained supernatant was added with 40% glycerol at 1:1, divided into sterile EP tubes, and stored at −20° C. A CPV-specific recombinant phage library was obtained.

2.2.5.2 Panning and Enrichment of CPV-Specific Recombinant Phages

The ELISA plate was coated with purified CPV as a target antigen, and the phage library rescued in 2.2.5.1 was panned for a total of 3 rounds, where a coating amount of the antigen was gradually reduced in each round, so as to screen the CPV-specific recombinant phage with a higher affinity. Specific operations were as follows:

(1) Plate coating with antigens: the purified CPV was diluted with a coating buffer to 100 μg/mL (for the first round of panning), 10 μg/mL (for the second round of panning) and 1 μg/mL (for the third round of panning), and then added to a 96-well ELISA plate separately at 100 μL/well, and placed at 4° C. overnight, the coating buffer was discarded, and the CPV was washed 5 times with PBST.

(2) Blocking: 300 μL of PBSM (PBS containing a 5% nonfat milk powder) was added to each well for blocking at 37° C. for 2 h; a blocking solution was discarded, the CPV was washed 5 times with PBST, spin-dried and stored at −20° C. for later use.

(3) Dilution of the recombinant phage library: 1 mL of the rescued recombinant phage library was diluted with 9 mL of PBSM, mixed well, and allowed to stand at 37° C. for 1 h.

(4) Binding: the diluted recombinant phage library was added to the coated ELISA plate at 100 μL/well, incubated with shaking at 37° C. and 80 rpm for 30 min, and then allowed to stand at 37° C. for 2 h.

(5) Washing away impurities: liquid was discarded in the well, the well was washed 5 times with PBST, and then washed 5 times with PBS, and the washing liquid was discarded, and spin-dried. In the second and third rounds of panning, the number of washes was increased accordingly to further reduce non-specific binding.

(6) Primary infection: 100 μL of a TG1 bacterial solution cultured to a logarithmic growth phase was added into each well, incubated at 37° C. for 20 min, and an obtained bacterial solution was collected.

(7) Elution: 200 μL of an eluate (200 mM glycine, pH 2.2) was added to each well, and shaken gently on a micro-shaker for 10 min.

(8) Neutralization: the eluate in the well was aspirated, and a 1 M Tris buffer (pH 9.0) was quickly added to adjust a pH value to 7.4, to restore the infection ability of the phage.

(9) Re-infection and amplification: the above eluate was added to 5 mL of the TG1 bacterial solution cultured to a logarithmic growth phase, mixed with the bacterial solution of primary infection, and allowed to stand at 37° C. for 2 h. The bacterial solution was added to 100 mL of the LB (Amp+) medium, and incubated by shaking at 37° C. for 4 h to 6 h, such that an $OD_{600}$ value of the bacterial solution reached 0.6 to 0.8.

(10) Rescue: the helper phage M13K07 was added, and rescue was conducted according to steps 2) to 6) of 2.2.5.1.

A supernatant after the pellets were resuspended was an amplified solution of the recombinant phage library obtained in the first round of panning, which was partially preserved, and the rest was subjected to the next round of panning, where the steps of the second and third rounds of panning were the same as those of the first round, referring to steps 3 to 10.

2.2.6 Detection of Phage Monoclonal 2.2.6.1 Preparation of Monoclonal

100 μL of a mixture of the second infestation during the third panning (step 9 in 2.2.5.2) was diluted by multiple times, spread on a solid LB (Amp+) medium plate, and incubated overnight at 37° C. upside down. A preparation method of the phage monoclonal included the following steps:

(1) An LB (Amp+) liquid medium was added to a 96-well deep-well plate at 800 μL/well, and 96 single colonies were randomly selected from the plate, added to the deep-well plate separately, and incubated overnight at 37° C. and 200 rpm with shaking. The obtained plate was used as a mother plate.

(2) Another 96-well deep-well plate was added with 800 μL of the LB (Amp+) liquid medium in each well, and 100 μL of bacterial solutions were pipetted from corresponding wells of the mother plate, inoculated into the new plate, and incubated at 37° C., 200 rpm with shaking for 2 h. This was used as a test plate. After inoculation, 50% glycerol was added to the mother plate at 600 μL/well, and then frozen at −20° C.

(3) The helper phage M13K07 was added to the incubated detection plate at an multiplicity of infection (MOI) of 20:1, allowed to stand in a 37° C. incubator for 30 min, and then incubated with shaking at 37° C. and 200 rpm for 30 min.

(4) The detection plate was placed in a rotor of the ELISA plate of a centrifuge, and centrifuged at 4,000 rpm for 20 min at room temperature, and a resulting supernatant was discarded; 800 μL of the LB (Amp+, Kana+) medium was added to each well to resuspend the cells, and the cells were incubated at 37° C., 200 rpm overnight.

(5) The detection plate was centrifuged again at 4° C. and 4,000 rpm for 40 min, a supernatant was aspirated from each well, and added to a new 96-well deep-well plate correspondingly to obtain a monoclonal of the phage, and stored at 4° C. for later use.

2.2.6.2 ELISA Detection of CPV-Specific Phage

The ELISA detection was conducted with the monoclonal of the above phage as a primary antibody, and a specific operation method included the followings:

(1) Plate coating: the purified CPV was diluted to 1 μg/mL with the coating buffer, added into a 96-well ELISA plate at 100 μL/well, and placed at 4° C. overnight, the coating buffer was discarded, and the CPV was washed 5 times with PBST.

(2) Blocking: 300 μL of PBSM (PBS containing a 5% nonfat milk powder) was added to each well for blocking at 37° C. for 2 h; a blocking solution was discarded, and the CPV was washed 5 times with PBST, spin-dried and stored at −20° C. for later use.

(3) 90 μL of PBSM was added to each well, and the phage monoclonal obtained in 2.2.6.1 was added to corresponding wells of the ELISA plate; a negative control plate with no antigen coating was set up in parallel, at 10 μL/well; after incubation at 37° C. for 2 h, the liquid in the wells was discarded, and the plates were washed 5 times with PBST.

(4) Secondary antibody incubation: 100 μL of a 1000-fold diluted HRP-labeled mouse anti-M13 antibody was added to each well, and incubated at 37° C. for 1 h, the secondary antibody was discarded, and the plates were wash 5 times with PBST.

(5) Color development: 100 μL of a TMB color development solution was added to each well for incubation in the dark for 15 min.

(6) Termination: 50 μL of a 2 M sulfuric acid solution was added to terminate the color development.

(7) Determination of results: an $OD_{450}$ value was measured, a ratio of average absorbance values of sample serum to negative serum >2.1 was determined as positive.

2.2.6.3 Positive Monoclonal Sequencing

According to the ELISA assay results, monoclonal with higher positive values were selected, and PCR amplification was conducted with universal primers of the pComb3x vector (Table 7). An amplification system and conditions were the same as those in Table 3 and Table 4. PCR products were sent to a company for sequencing, and sequencing results were analyzed using DNAMAN software.

TABLE 7

Universal primers of pComb3x vector

| Primer | Primer sequence (5'→3') |
|---|---|
| pComb3x-F | AAGACAGCTATCGCGATTGCAG (SEQ ID NO: 7) |
| pComb3x-R | GCCCCCTTATTAGCGTTTGCCATC (SEQ ID NO: 8) |

2.3 Results and Analysis
2.3.1 Propagation and Purification of CPV

Figure 2:
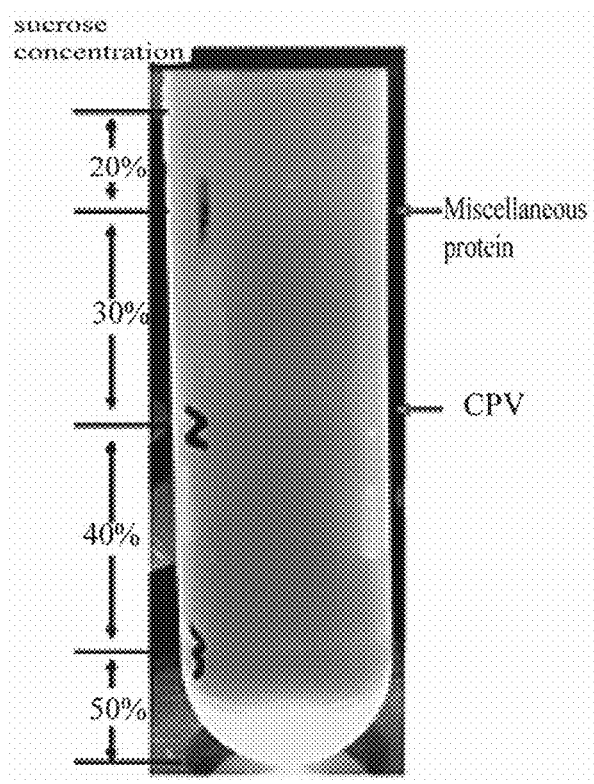

After the CRFK cells were inoculated with a TS02 strain CPV-2c virus, the CPE was clearly observed after incubation at 37° C. for 72 h. About 96 h after inoculation, when the CPE reached 80% to 90% (FIG. 1A), the inoculated cells were harvested and frozen and thawed at −20° C. 3 times. The supernatant was collected after centrifugation at 4° C., 8,000 rpm for 5 min. A cell culture supernatant was subjected to ultrafiltration, ultracentrifugation and sucrose density gradient separation to obtain a purified CPV. As shown in FIG. 2, after a concentrated cell culture supernatant was centrifuged by sucrose density gradient, two main protein bands were seen; after the bands were collected separately, it was determined that the CPV was mainly concentrated in the sucrose density gradient of 30% to 40% detected by CPV antigen detection test strips. The purified virus suspension had a protein concentration of about 1.2 mg/mL as determined by a UV spectrophotometer.

Figure 3A:
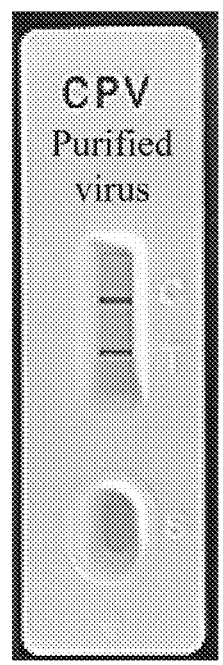
Figure 3B:
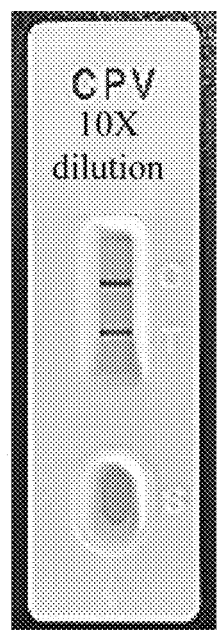
Figure 3C:
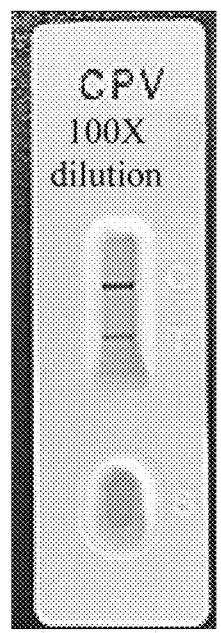
Figure 3D:
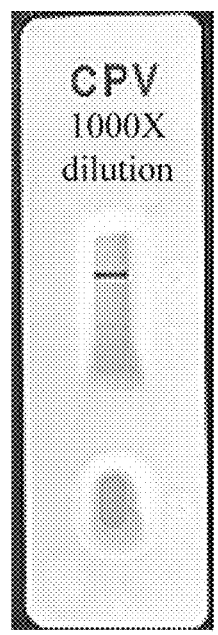
Figure 4:
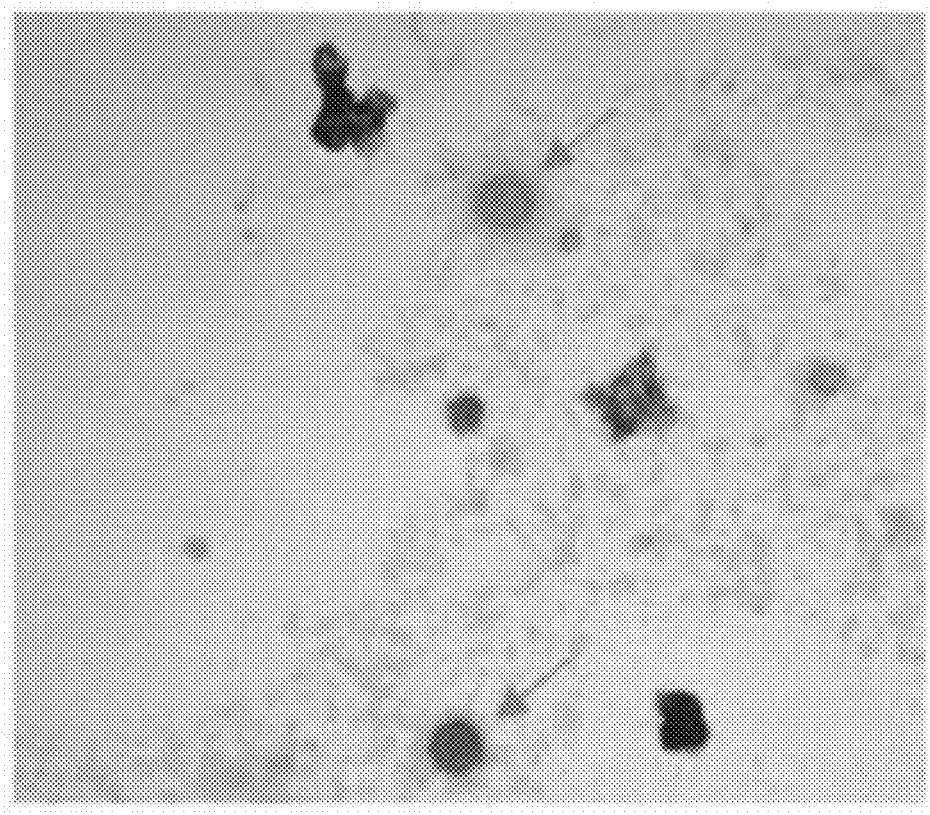

The purified CPV was diluted 10 times, 100 times and 1,000 times separately, and detected with the CPV antigen detection test strips, with a sample volume of 100 μL. The results showed that after the purified virus was diluted 1,000 times, the antigen detection line was still visible (FIG. 3D), and the virus antigen detection line was obvious after 10 to 100 times of dilution, indicating that the purified CPV particles had a high degree of enrichment. After a small amount of purified CPV was negatively stained, CPV particles (about 20 nm to 30 nm in diameter) were quickly found by electron microscope observation. As shown in FIG. 4, there were fewer heteroproteins other than virions. Therefore, the purified CPV could be used as an antigen to construct a CPV-specific phage library.

2.3.2 Antibody Levels After Immunization

The peripheral blood of the immunized alpaca was collected 14 days after the third and fourth immunizations separately, the serum was separated, and a CPV antibody level was determined by indirect ELISA. The serum was diluted to 1,000 times, 5,000 times, 25,000 times and 125,000 times separately and used as a primary antibody, and then added to the ELISA plate coated with CPV; meanwhile, a negative serum of non-immunized alpaca was used as a negative control, and Goat Anti-Alpaca IgGH&L (HRP) was used as a secondary antibody; finally, if the $OD_{450}$ value of a sample to be tested to the $OD_{450}$ value of the negative serum had a ratio of greater than 2.1, the dilution was determined to be positive, and a highest dilution with a positive test result was used as a CPV antibody titer of the serum. The $OD_{450}$ value determination results are shown in Table 8, and the antibody titer results are shown in FIG. 5. It was seen from the figures that the serum titer after the third and fourth immunizations reached 1:25000, and this antibody level was suitable for preparation of the immune antibody library.

TABLE 8

ELISA experiment data

| | Serum dilution factor and mean $OD_{450nm}$ | | | |
|---|---|---|---|---|
| Group | 1:1000 | 1:5000 | 1:25000 | 1:1250000 |
| Third immunization serum | 1.0910 | 0.7170 | 0.2590 | 0.0800 |
| Negative serum | 0.1580 | 0.0710 | 0.0480 | 0.0440 |
| Fourth immunization serum | 1.318 | 0.995 | 0.463 | 0.135 |
| Negative serum | 0.371 | 0.16 | 0.083 | 0.067 |

2.3.3 PCR Amplification Results of VHH Gene

Figure 6A:
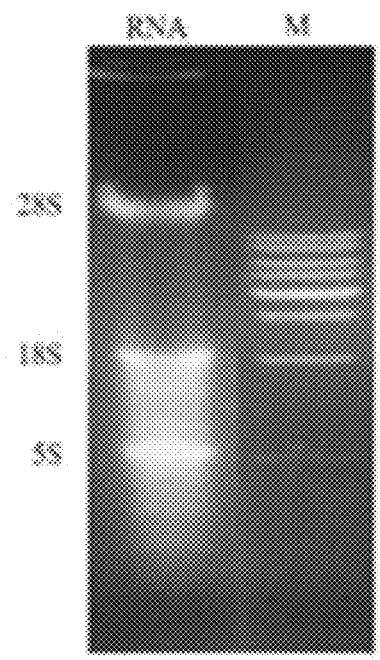
Figure 6B:
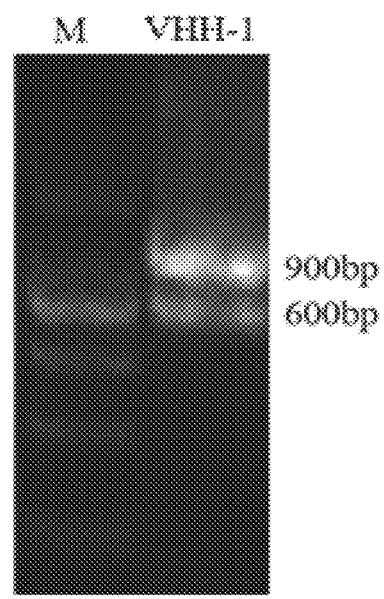
Figure 6C:
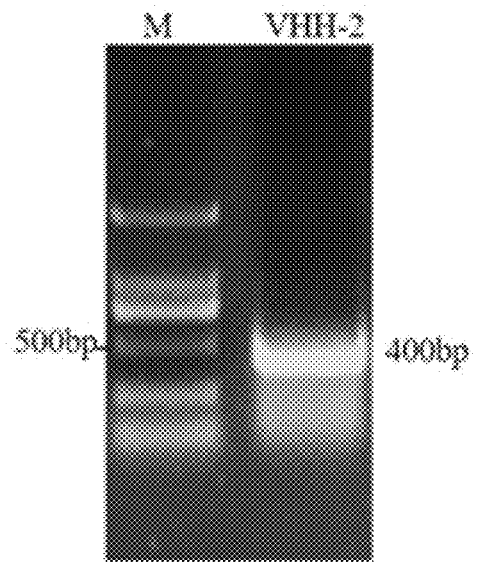

About 30 mL of alpaca peripheral blood was collected on the 14th day after the fourth immunization, and lymphocytes were separated according to instructions of a lymphocyte isolation kit; the RNA in lymphocytes was extracted by a Trizol method, and the RNA extraction results are shown in FIGS. 6A-C. As shown, the extracted RNA samples had distinct 28S and 18S bands at 5 K and 2 K (FIG. 6A), indicating that the RNA was of desirable quality and could be used for the amplification of VHH sequences. After the RNA was reverse-transcribed, two bands at 600 bp and 900 bp were visible in the amplification product of the first round of PCR primers (FIG. 6B); after the second round of amplification using the above amplification product as a template, the product had an obvious band at 400 bp (FIG. 6C), which was in line with the expected size of the VHH fragment.

Figure 7:
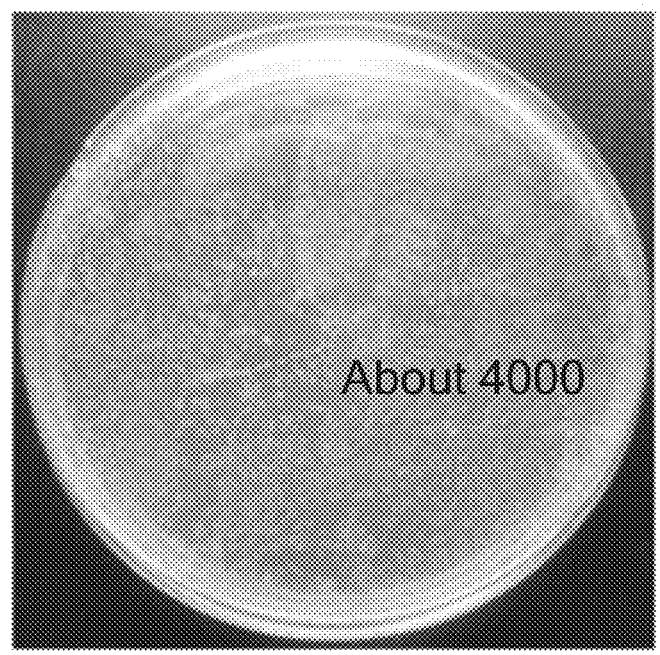

2.3.4 Identification Results of the Initial Antibody Library
2.3.4.1 Library Capacity of the Initial Antibody Library The VHH target fragment amplified in the second round was recovered, and ligated to the pComb3x vector by enzyme digestion, and the TG1 competent cells were electroporated to obtain the initial VHH library. 10 µL of the bacterial solution of the initial antibody library was diluted 1,000 times, 200 µL of a diluted bacterial solution was coated on the LB (Amp+) plate, and incubated overnight at 37° C. upside down; the number of colonies on the plate was counted the next day about 4,000 (FIG. 7), and the library capacity of the initial antibody library was calculated to be about $2.0 \times 10^6$ CFU/mL. The library capacity was in line with the expected library capacity of the immune library and could be used for specific phage panning.

Figure 8:
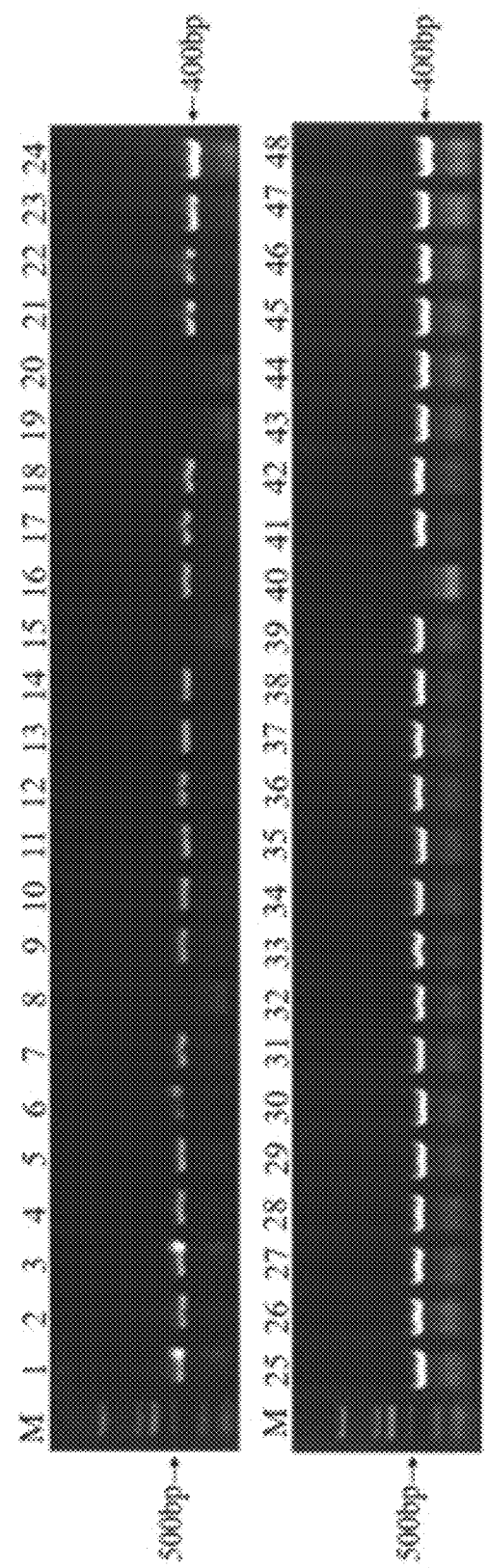

2.3.4.2 Positive Rate of Initial Antibody Library 48 single colonies were randomly selected from the colony plate for the above library capacity determination, added into 500 µL of the LB (Amp+) medium, and incubated with shaking at 37° C. and 200 rpm for 4 h; a product was used as a template to amplify the VHH gene with specific primers. The results of gel electrophoresis of PCR products are shown in FIG. 8, where there were 43 positive samples and 5 negative samples, and the recombination rate was about 89.6%.

2.3.4.3 Diversity of the Initial Antibody Library

The amino acid sequences of 20 positive monoclonals were aligned and analyzed by DNAMAN software. The results showed that the homology of the 20 VHH genes was 78.9%, and a CDR3 region had large differences, indicating that the heavy-chain variable region gene in the initial library had a desirable diversity. A phylogenetic tree of the sequences was plotted by MEGA software, and it was found that the homology differences between the sequences were relatively large, further indicating that the initial library had desirable diversity, and could be used for the screening of specific phages.

2.3.5 Phage Monoclonal Detection and Sequencing Results

The bacterial solution infected by the phage after the third round of panning was diluted in multiple proportions with the LB medium, spread on a solid LB (Amp+) plate medium, and cultured upside down at 37° C. overnight; the next day, 96 monoclonals were randomly selected from the plate and used as primary antibodies after proliferation for ELISA detection. The results showed that 59 of the 96 monoclonals were CPV-specific positive clones, accounting for 61.5%, and a maximum P/N value could reach 22. It indicated that after three rounds of panning, the high-affinity recombinant phage that could specifically bind to CPV was effectively enriched.

2.3.6 Monoclonal Sequencing

Figure 9:
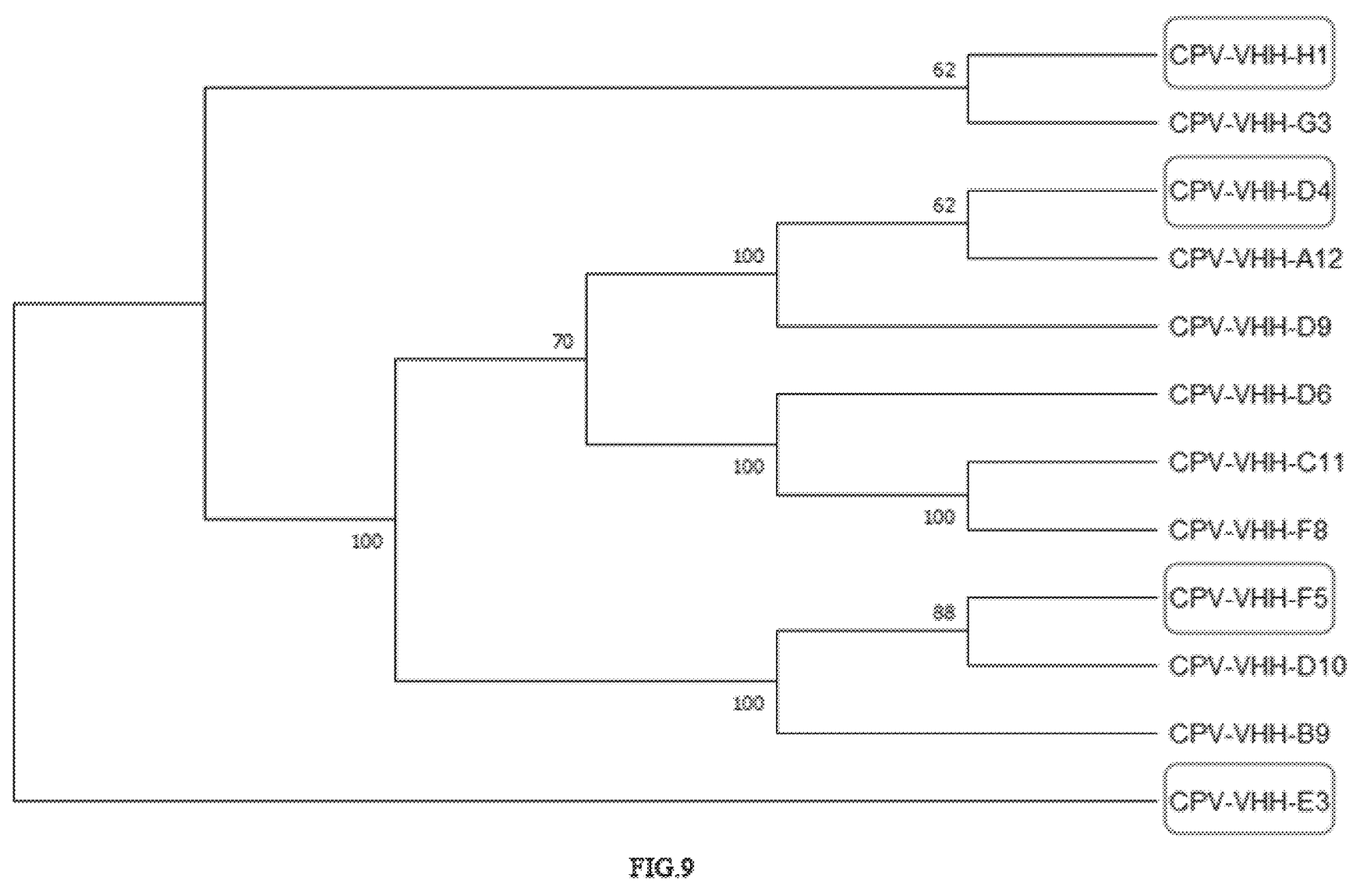

The bacterial solutions of the first 12 monoclonal strains with a higher P/N value in the ELISA screening were sent to gene company for sequencing, and the sequences were compared and analyzed, and a phylogenetic tree was plotted (FIG. 9); four sequences with the greatest differences, namely CPV-VHH-H1, CPV-VHH-D4, CPV-VHH-F5, and CPV-VHH-E3, were selected for VHH expression and identification.

Example 2 Expression and Identification of CPV Nanobodies

1. Experimental Materials
1.1 Cells, Vectors and Virus Seeds

HEK293F cells, CRFK cells, pcDNA3.1 vector and CPV-2c strain (TS02 strain, F15 generation, $10^{6.5}$ TCID$_{50}$/1 mL) were provided by Institute of Animal Sciences of Chinese Academy of Agricultural Sciences. DH5α competent cells were purchased from TransGen Biotech (Beijing).

1.2 Solution Preparation

1) PEI solution (1 mg/mL): 100 mg of a PEI powder was added to 90 mL of ultrapure water, HCl was slowly added while stirring to adjust the pH value to less than 2.0, and stirring was continued for 3 h to 4 h until completely dissolved. After complete dissolution, NaOH (10 mol/L) was slowly added dropwise to adjust the pH value to 7.0, and the solution was diluted to 1 L with a graduated cylinder. The solution was sterilized by filtration through a 0.22 µm needle filter and then dispensed into 1.5 mL centrifuge tubes, at 1 mL per tube, and stored at −80° C. for later use. After thawed, the solution can be stored at 4° C. for 30 d, avoiding repeated freezing and thawing.

2) Protein purification solution:
Binding Buffer: 20 mM Tris, 500 mM NaCl, 20 mM imidazole, pH adjusted to 8.0 with hydrochloric acid;
Wash Buffer: 20 mM Tris, 500 mM NaCl, 60 mM imidazole, pH adjusted to 8.0 with hydrochloric acid;
Elution Buffer: 20 mM Tris, 500 mM NaCl, 500 mM imidazole, pH adjusted to 8.0 with hydrochloric acid.

3) Protein gel staining solution: 1 g of Coomassie brilliant blue G250 was completely dissolved by stirring in 1 L of a solution containing 25% isopropanol and 10% glacial acetic acid.

4) Protein gel decolorization solution: 100 mL of acetic acid and 50 mL of absolute ethanol were added to 850 mL of deionized water, and mixed well.

5) 5×SDS-PAGE running buffer: 15.1 g of Tris, 94 g of glycine, and 5 g of SDS were diluted to 1 L with deionized water. The buffer was diluted 5 times with deionized water before use.

2. Experimental Methods
2.1 Construction of VHH Recombinant Expression Vector
2.1.1 Primer Design According to sequences of the 4 phage strains panned, universal primers with Xma I and Xho I restriction sites were designed and synthesized, and a 6×His tag sequence was added to an N-terminal of an antibody sequence. The primer sequences were as follows:

```
VHH-F:
5'-GGTGGTGTACATCTCCTACATCTACGCCCCCGGGCAGGTGCAGCT
GGTGGAGTC-3' (SEQ ID NO: 9, the underlined part
was the restriction site of Xma I);

VHH-R:
5'-ATGGTGATGGTGGTGCTCGAGTTAGTGGTGGTGGTGGTGAGA
GGAGACGGTGACCT-3' (SEQ ID NO: 10, the underlined
part was the restriction site of Xho I).
```

2.1.2 Amplification of the Target Gene

The plasmid DNAs extracted from the 4 strains were used as templates for PCR amplification. The reaction system and procedures are shown in Table 9 and Table 10, and the amplification products were detected by 1% agarose gel electrophoresis.

TABLE 9

PCR amplification system

| Reagent/sample | Volume (μL) |
| --- | --- |
| Template | 2 |
| VHH-F and VHH-R | Each 2 |
| 2 × Phanta Max MasterMix | 25 |
| ddH$_2$O | 19 |
| Total Volume | 50 |

TABLE 10

Amplification process of PCR

| Process | Reaction temperature (° C.) | Reaction time |
| --- | --- | --- |
| Pre-denaturation | 95° C. | 5 min |
| Denaturation | 95° C. | 30 s |
| Annealing | 56° C. | 30 s |
| Extension | 72° C. | 1 min |
| Re-extension | 72° C. | 5 min |
| Storage | 4° C. | ∞ |

2.1.3 Enzyme Digestion, Ligation and Transformation

The DNA of the target fragment was recovered according to instructions of an agarose gel recovery kit, and the nucleic acid concentration was measured by UV spectrophotometer. The recovered target fragment and the pcDNA3.1 vector were double-digested with Xma I and Xho I enzymes respectively. The enzyme digestion reaction system is shown in Table 11. After mixing, the components were briefly centrifuged to the bottom of the tube and placed at 37° C. for digestion overnight.

TABLE 11

Double enzyme digestion reaction system

| Reaction Component | Volume |
| --- | --- |
| Xma I and Xho I | Each 1 μL |
| 10 × CutSmart Buffer | 5 μL |
| VHH target fragment/pcDNA3.1 vector | 1 μg |
| ddH$_2$O | Up to 50 μL |
| Total Volume | 50 μL |

After the digestion reaction, nucleic acid electrophoresis detection was conducted, the target fragment was recovered, and the VHH gene fragment and the pcDNA3.1 vector were ligated with the T4 DNA ligase. The ligation reaction system is shown in Table 12. Each component was added to a 1.5 mL EP tube, centrifuged briefly to the bottom of the tube, and ligated at 37° C. for 30 min.

TABLE 12

T4 DNA ligase ligation system

| Reaction Component | Volume |
| --- | --- |
| T4 DNA Ligase | 1 μL |
| 10 × T4 DNA Ligase Buffer | 1 μL |
| Target fragment and vector recovered after enzyme digestion | Fragment and vector have a molar ratio of approximately 1:3 |
| ddH$_2$O | Up to 10 μL |
| Total Volume | 10 μL |

The ligation product was transformed into DH5α competent cells; the next day, 12 monoclonals were selected from the plate and placed into EP tubes containing 500 μL of LB (Amp+) medium, and incubated with shaking at 200 rpm for 4 h; the positive rate of transformation was determined by universal vector primers, and 3 positive bacterial solutions were selected from each group and sent to a company for sequencing. According to the sequencing results, the strains with correct sequence ligation and no mutation were selected to extract the plasmid DNA of the recombinant expression vector for VHH gene expression.

2.2 Transient Expression of VHH in HEK293F

HEK293F cells were resuscitated, incubated with shaking at 37° C., 5% CO$_2$, and 140 rpm for 2 d to 3 d and passaged once; a density should reach 3.0×10$^6$ cells/mL during passage, and an initial density after passage should be (0.3–0.5)×10$^6$ cells/mL. After resuscitation, the cells should be passaged for at least 2 times to stabilize the cell state, and the cells were used for transfection experiments when a survival rate was more than 98%.

The HEK293F cells were transfected by the following method:

(1) One day before transfection, the HEK293F cells that had been cultured for 2 d to 3 d were counted, and a cell density was adjusted to 1.5×10$^6$ cells/mL. The amount of fresh medium added should be greater than 50% of the final volume, which could be achieved by cell centrifugation and replacement with fresh medium.

(2) On the day of transfection, the cells were counted, adjusted to a density of 2.0×10$^6$ cells/mL with fresh medium, and distributed into 6-well cell culture plates, at 2.5 mL/well.

(3) An appropriate amount of plasmid DNA and PEI solution was pipetted to 300 μL of an Opti-MEM medium separately, such that the final concentration of DNA during transfection was 1 μg/mL, and the final concentration of PEI was 5 μg/mL; the diluted DNA was sterilized by filtration through a 0.22 μm filter, mixed with the diluted PEI solution, allowed to stand at room temperature for 20 min, and then slowly added to the prepared cells in each well.

(4) Meanwhile, the pcDNA3.1-EGFP vector was used as a control plasmid for transfection under the same conditions.

After transfection, the cells were incubated with shaking at 37° C., 5% CO$_2$, and 140 rpm for 7 d, during which an appropriate amount of a fresh medium was added according to the cell state. After the cultivation, the cell culture medium was collected, and the cells and cell debris were removed by centrifugation at 8,000 rpm for 5 min. A cell culture supernatant was harvested; a small amount of the supernatant was collected for SDS-PAGE electrophoresis to detect the expression of the target protein, and the remaining samples were stored at −20° C.

2.3 Purification of VHH

2.3.1 Affinity Purification with Ni-Magnetic Beads

The target protein with 6×His tag was purified by the affinity purification method with Ni-magnetic beads. The specific purification steps were as follows:

(1) 2 times the volume of the Binding buffer was added to the cell culture supernatant and mixed well, added with 1% volume of Ni-magnetic beads, shaken at 80 rpm for adsorption for 2 h, and placed on a magnetic stand to separate the magnetic beads, and a supernatant was discarded;

(2) the magnetic beads were washed 3 times with 5 times a loading volume of the Wash Buffer to remove impurities as much as possible; and (3) the Elution Buffer was added at $1/20$ times a volume of the original cell supernatant, and eluted at room temperature for 10 min to 30 min, and an eluate was collected.

2.3.2 Liquid Exchange, Concentration and Detection of Purified Protein

The purified antibody protein was exchanged with an ultrafiltration tube in a molecular weight cut-off of 3 kD, and the Elution Buffer containing imidazole was exchanged with 20 mM Tris-HCl (pH 8.0), and concentrated.

2.3.3 Identification of VHH

The purified antibody protein was identified by SDS-PAGE electrophoresis, indirect ELISA, indirect immunofluorescence (IFA) and CPV neutralization assay (VN).

2.3.4 SDS-PAGE Electrophoresis Detection

The concentration and purity of the purified antibody protein were detected by SDS-PAGE electrophoresis. 30 μL of each of the purified protein solution and the cell culture supernatant were added with 10 μL of a 4× Loading Buffer separately, centrifuged briefly and placed in boiling water for 10 min. The prepared SDS-PAGE gel plate was placed in a vertical electrophoresis tank, and added with an appropriate amount of an electrophoresis buffer. The prepared sample and protein marker were added to the wells of the gel plate, at 10 μL/well. The electrodes of the electrophoresis tank were connected correctly, and electrophoresis was conducted at a constant voltage of 180 V, and terminated when bromophenol blue migrated to the bottom of the gel plate. The gel was transferred in an appropriate amount of a protein glue staining solution, and shaken slightly for about 30 min of staining, and then the staining solution was rinsed with water; an appropriate amount of a protein gel decolorization solution was replaced, and shaken to decolorize until the background was transparent and clear.

2.3.5 Indirect ELISA Detection

The indirect ELISA detection included the steps as follows:

1) Antigen coating: the purified CPV was diluted to 10 μg/mL with the coating buffer, a diluted CPV antigen solution was added to the ELISA plate, at 100 μL/well, and placed at 4° C. overnight, the coating solution was discarded, and the plate was rinsed with PBST 5 times.

2) Blocking: 300 μL of PBSM (PBS containing a 5% nonfat milk powder) was added to each well, and blocked at 37° C. for 2 h; a blocking solution was discarded, the CPV was washed 5 times with PBST, and spin-dried.

3) Primary antibody incubation: the purified nanobody was diluted with 5% PBSTM (dilution factors were 1:10, 1:100, 1:1000 and 1:10000, respectively); a diluted antibody was added to the ELISA plate, at 100 μL/well, where 3 parallel groups were made for each dilution, and a negative control was set up at the same time. The antibodies were incubated at 37° C. for 1 h, washed 5 times with PBST, and spin-dried.

4) Enzyme-labeled secondary antibody incubation: an anti-His-HRP antibody was diluted at 1:3000 with 5% PBSTM, at 100 μL/well, incubated at 37° C. for 1 h, the secondary antibody was discarded, and the well was washed 5 times with PBST, and spin-dried.

5) TMB color development: 50 μL of the TMB color development solution was added to each well for incubation in the dark for 15 min.

6) Termination: 50 μL of a 2 M sulfuric acid solution was added to terminate the color development.

7) Determination of results: the 0D450 value was determined with a microplate reader.

2.3.6 IFA Detection

The IFA included the steps as follows:

(1) Cell plating and virus inoculation: a bottle of CRFK cells (T75) that had grown to a monolayer was digested, ¼ of the cell suspension was added to 20 mL of the DMEM medium containing 5% FBS, mixed well and spread to a 48-well cell plate, at 200 μL/well. The CPV seed virus was diluted by 20-fold, and added to the above cells at 100 μL/well. The plate was sealed and incubated at 37° C. in 5% $CO_2$ for 72 h.

(2) Fixation: a cell culture supernatant was discarded, and pre-cooled absolute ethanol was slowly added at 100 μL/well for incubation at 4° C. overnight.

(3) Blocking: the fixative was discarded, and the well was washed 3 times with PBST, at 600 μL/well and 2 min in each time, blocked with PBSTM containing 5% nonfat dry milk as a blocking solution at 37° C. for 1 h at 400 μL/well, and washed 3 times with PBST.

(4) Primary antibody incubation: the purified nanobody was diluted by 10 times with 5% PBSTM, the diluted nanobody was added to the ELISA plate, at 100 μL/well, and a CPV mouse polyclonal antibody positive control (1:10 dilution) and negative control were set up. The antibodies were incubated at 37° C. for 1 h, washed 5 times with PBST.

(5) Secondary antibody incubation: the anti-His-FITC antibody was diluted by 1:1000-fold with 5% PBSTM, and added at 100 μL/well; the CPV mouse polyclonal antibody positive control wells were added with 1:1000-fold dilution of anti-mouse-FITC as the secondary antibody for incubation at 37° C. for 1 h in the dark; after 5 times of washing, 200 μL of PBST was added to each well to keep moist, and the plate was stored at 4° C. in the dark.

(6) the experimental results were observed under a fluorescence microscope.

2.3.7 Virus Neutralization Antibody Detection (VN)

The CPV neutralization assay was conducted as follows:

(1) Dilution of nanobodies: the purified recombinant expressed nanobodies were diluted 5 times with DMEM, filtered and sterilized through a 0.22 μm syringe filter, and added to the first row of a 96-well cell plate, at 100 μL per well; the antibodies were serially diluted by 2-fold (100 μL+100 μL) to 1:640, with 3 replicates for each dilution, and virus control and uninfected normal cell control wells were set up at the same time.

(2) Virus dilution: CPV-2C cell virus (F15 generation, 10 6.5 $TCID_{50}$/mL) was diluted 30,000 times with DMEM (about 100 $TCID_{50}$ per 100 μL), and added to the cell wells with the diluted antibody, at 100 μL/well. The above diluted virus solution was further diluted 10 times serially to $10^{-1}$, $10^{-2}$ and $10^{-3}$, which contained 10, 1 and 0.1 $TCID_{50}$, respectively, and were added to cell wells without antibodies as a virus regression experiment, at 100 μL per well, with 5 wells for each dilution.

(3) Neutralization: the cell plate was shaken and mixed for 10 sec, incubated at 37° C. for 1 h, and mixed every half hour.

(4) Adding cells: the digested cell suspension (containing 15% FBS) was added into the neutralized cell wells, at 60 μL per well.

(5) Culture observation: the cell plate was placed in an incubator containing 5% $CO_2$ at 37° C. for 7 d to observe the cytopathic condition.

3. Results and Analysis 3.1 Construction of VHH Recombinant Expression Vector

Figure 10:
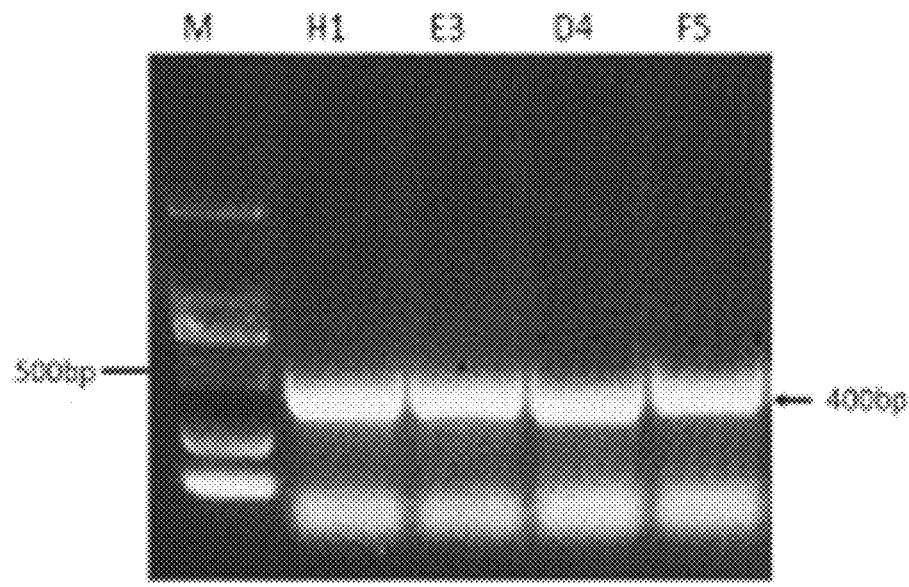
Figure 11:
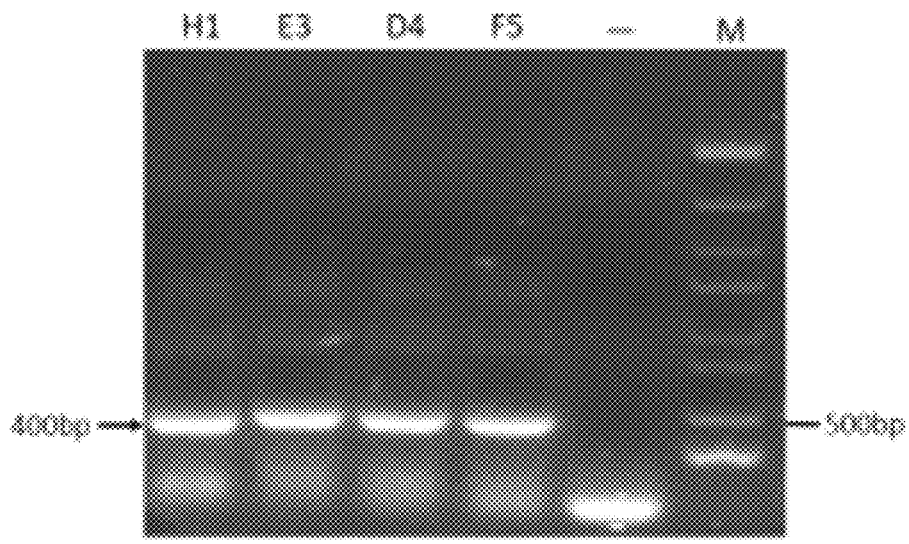

Specific primers were designed according to the sequences of the 4 phage strains selected by panning, namely CPV-VHH-H1, CPV-VHH-E3, CPV-VHH-D4 and CPV-VHH-F5, and 4 VHH fragments with a size of about 400 bp were amplified (FIG. 10), which were in line with the expected results. The fragments recovered from the gel and the pcDNA3.1 vector constructed in the laboratory (with the addition of melittin signal peptide and Xma I restriction site) were double-digested with Xma I and Xho I enzymes, respectively. The product of enzyme digestion is shown in FIG. 11. A gel with a size of about 400 bp was cut, and the target fragment was recovered according to instructions of a gel recovery kit.

Figure 12:
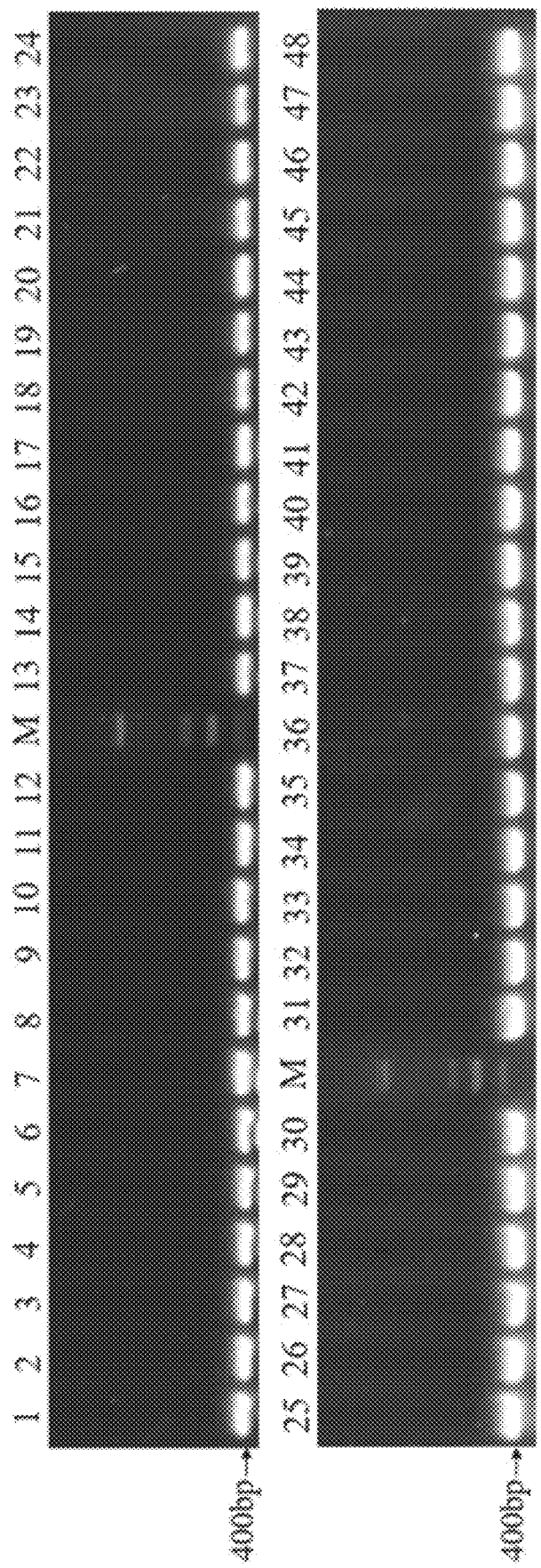

The digested fragment and vector were ligated with a T4 ligase and transformed into DH5α competent cells; the next day, 12 single colonies were randomly selected from each group, and specific primers were used to amplify the target fragment after expanding propagation; the detection of PCR products by gel electrophoresis showed that all single colonies were positive, and a positive rate of transformation was 100% (FIG. 12).

The 3 positive clones randomly selected from each group were sent to a sequencing company for sequencing, and the sequencing results were aligned by DNAMAN. The sequences of at least 2 of the 3 clones submitted for inspection in each group were correctly ligated without mutation, proving that the recombinant expression vector pcDNA3.1-VHH of the 4 strains of nanobodies had been successfully constructed, and the recombinant nanobodies could be expressed in mammalian cells.

3.2 Transient Expression of VHH

Figure 13:
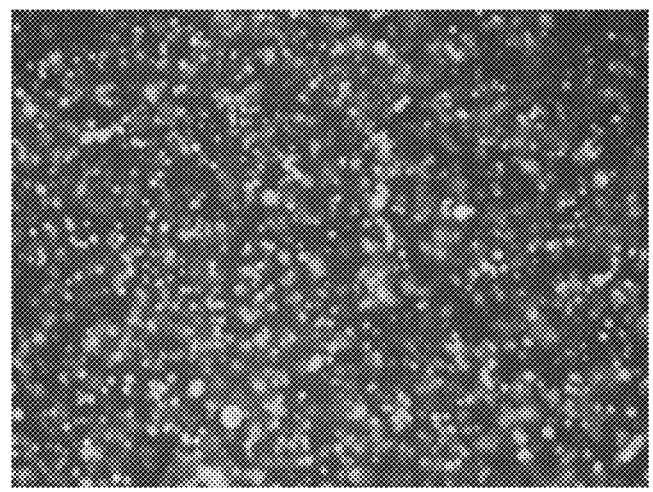
Figure 14:
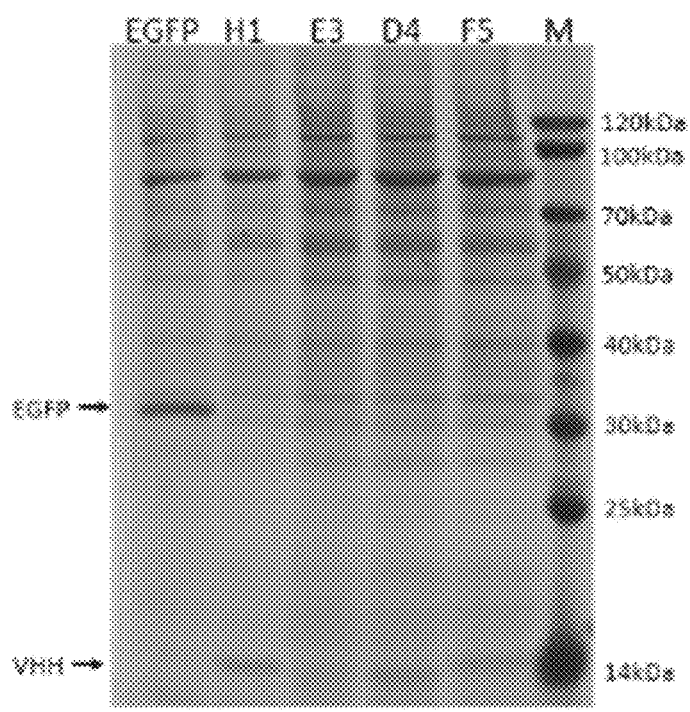

The transfection effect of the control plasmid was observed by fluorescence microscope on the second day after transfection. Referring to FIG. 13, the number of fluorescent/non-fluorescent cells was counted, and the transfection efficiency was calculated to be approximately 50%. A cell supernatant was harvested on the 7th day after transfection and detected by SDS-PAGE electrophoresis. The target protein band was about 14 kD in size, but had a low expression level, and an obvious EGFP control protein band with a size of about 30 kD was seen (FIG. 14).

3.3 Purification of VHH

Figure 15:
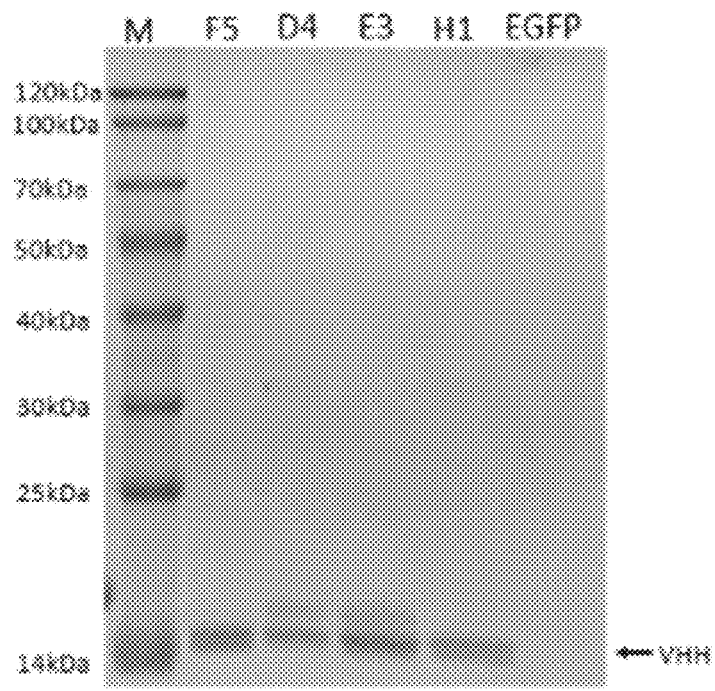
Figure 16A:
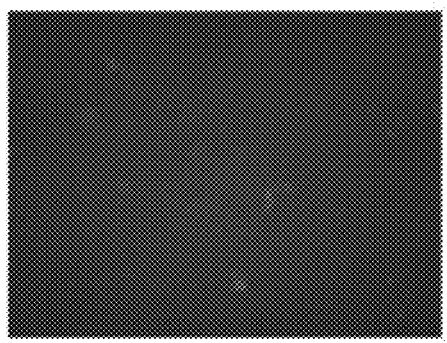
Figure 16B:
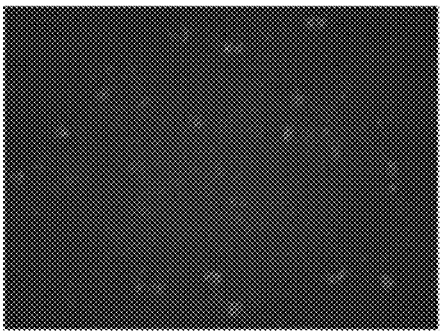
Figure 16C:
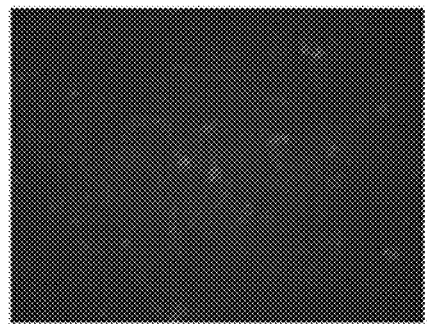
Figure 16D:
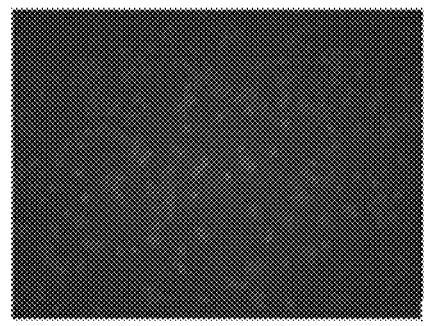
Figure 16E:
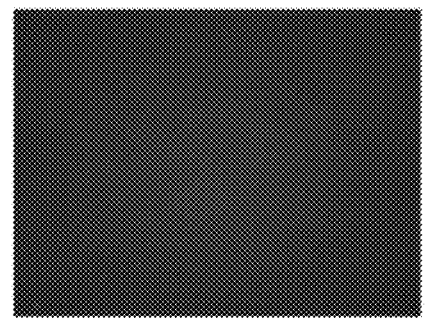
Figure 16F:
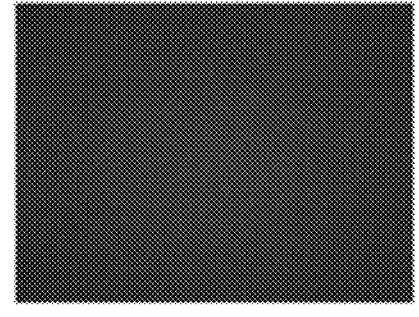

The cell culture supernatants of the four groups of recombinant VHH and the control cell culture supernatant expressing EGFP were all subjected to affinity purification with Ni-magnetic beads. The purified sample showed an obvious VHH target band (FIG. 15), about 15 kDa in size, and the protein purity was greater than 90%. The control protein was not enriched by Ni-magnetic beads, and the results were in line with expectations.

The above experiments proved that four nanobodies, CPV-VHH-H1, CPV-VHH-E3, CPV-VHH-D4 and CPV-VHH-F5, had been successfully expressed, and the recombinant nanobody protein could be efficiently enriched by tagging protein 6×His.

3.4 Identification of VHH 3.4.1 Indirect ELISA Test Results

The specificity of the four nanobodies expressed was identified by indirect ELISA, and a ratio of the $OD_{450\ nm}$ value of the experimental group to that of the control group of greater than 2.1 was determined as positive (Wang Zhaoyang et al., 2020). The results showed that the reactivity of the four nanobodies with the virus was still significantly higher than that of the negative control after being diluted 1000 times, indicating that the four nanobodies could specifically bind to CPV. The ELISA results are shown in Table 13.

TABLE 13

Indirect ELISA experimental data

| Group | Antibody dilution factor and mean $OD_{450nm}$ | | | | Result determination |
|---|---|---|---|---|---|
| | 1:10 | 1:100 | 1:1000 | 1:10000 | |
| CPV-VHH-H1 | 2.56 | 2.46 | 0.28 | 0.10 | Positive (+) |
| CPV-VHH-E3 | 2.81 | 2.60 | 2.24 | 0.17 | Positive (+) |
| CPV-VHH-D4 | 2.87 | 2.64 | 2.29 | 0.27 | Positive (+) |
| CPV-VHH-F5 | 3.07 | 2.81 | 2.06 | 0.22 | Positive (+) |
| Negative control group | 0.07 | | | | |

3.4.2 Experimental Results of IFA

The specificity of the four nanobodies to CPV was verified by indirect immunofluorescence experiments. Since the recombinant nanobodies had 6×His tags, if the nanobodies could specifically bind to CPV, the fluorescent signal could be seen using an anti-His tag antibody with a FITC tag as a secondary antibody. The results showed that the 4 recombinant nanobodies could specifically bind to CPV, and the IFA results are shown in FIGS. 16A-F.

3.4.3 Virus Neutralization Assay Results (VN)

The neutralization activity of the expressed recombinant nanobodies was detected by neutralization assay (VN) for CPV. It was showed that the neutralization titers of the four nanobodies against CPV were all less than 1:10, and it was preliminarily determined that the four VHHs did not have CPV neutralization activity. The neutralization antibody titer determination results are shown in Table 14.

TABLE 14

Virus neutralization assay results

| Group | Antibody dilution factor and CPE number | | Virus regression experiment | |
|---|---|---|---|---|
| | 1:10 | >1:10 | Dilution | CPE number |
| CPV-VHH-H1 | 3/3 (+) | All (+) | 1 ($100TCID_{50}$) | 5/5 (+) |
| CPV-VHH-E3 | 3/3 (+) | All (+) | $10^{-1}$ ($10TCID_{50}$) | 4/5 (+) |
| CPV-VHH-D4 | 3/3 (+) | All (+) | $10^{-2}$ ($1TCID_{50}$) | 1/5 (+) |
| CPV-VHH-F5 | 3/3 (+) | All (+) | $10^{-3}$ ($0.1TCID_{50}$) | 0/5 (+) |
| Normal cell control | 0/5 (+) | | | |
| Virus control | 5/5 (+) | | | |

Note:
"(+)" indicated that CPE appeared in cell wells.

In the present disclosure, the biological characteristics of the four recombinant nanobodies were identified through experiments such as SDS-PAGE, ELISA, IFA, and the determination of the neutralization titer of CPV. The results showed that the four nanobodies expressed by HEK293F cells could specifically bind to CPV, but did not have the neutralization activity against the CPV-2c strain. The possible reasons for the analysis are: (1) the VHH screened by the whole virus in this experiment is not an antibody that recognizes the key sites of virus-infected cells. The VP2 protein is the immunogenic protein of CPV, which includes neutralization antigenic sites. The CPV VP2 protein can be used as a target antigen to conduct more targeted specific screening of the phage library, or to obtain nanobodies with neutralization activity (XU et al., 2014). (2) Due to an extremely low molecular weight, the nanobody is beneficial to bind the antigen site, but it is not enough to form an effective steric hindrance effect to block the ability of the virus to infect cells. Nanobodies can be modified by some means of genetic engineering, such as constructing multimers or bispecific antibodies through flexible linking peptides in series with nanobodies, so as to improve the function of nanobodies.

In addition, due to the high specificity of CPV, it is possible to apply the expressed recombinant nanobodies to the research of CPV diagnosis, such as rapid diagnosis of diseases, antibody labeling, and virus localization.

The foregoing examples are only intended to describe the preferred embodiments of the present disclosure and not intended to limit the scope of the present disclosure. Various alterations and improvements made by a person of ordinary skill in the art based on the technical solution of the present disclosure without departing from the design spirit of the present disclosure shall fall within the protection scope determined by the claims of the present disclosure.

```
                      Sequence Listing Information:

DTD Version: V1_3

File Name: GWP20220700544-sequence listing.xml

Software Name: WIPO Sequence

Software Version: 2.1.2

Production Date: 2022 Aug. 13

General Information:

Current application/IP Office: CN

Current application/Applicant file reference: GWP20220700544

Earliest priority application/IP Office: CN

Earliest priority application/Application number: 202111337157.X

Earliest priority application Filing date: 2021 Nov. 12

Applicant name: Institute of Animal Sciences of Chinese Academy of
Agricultural Sciences Applicant name/Language: en Invention title: CANINE PARVOVIRUS (CPV) NANOBODY CPV-VHH-H1 AND USE THEREOF (en)

Sequence Total Quantity: 10

Sequences:

SEQ ID NO: 1
Length: 128
Molecule Type: AA
Features Location/Qualifiers:
source, 1 . . . 128
mol_type, protein
note, Amino acid sequence of the heavy-chain variable region sequence
of the nanobody
organism, synthetic construct Residues:
QVQLVESGGG LAQPGGSLRL SCAASGAIDS ISAMRWFRQP PGKQRAVVAS ITSDGVTTYA      60
DSVKGRFTIS RDNAENTLYL QMNSLKTEDT GVYYCYAALK GYSSGVVAAS WGQGTQVTVS     120
GAHHSEDP                                                             128

SEQ ID NO: 2
Length: 384
Molecule Type: DNA
Features Location/Qualifiers:
source, 1 . . . 384
mol_type, other DNA
note, DNA sequence of the gene encoding the nanobody CPV-VHH-H1
organism, synthetic construct
```

Sequence Listing Information:

Residues:
```
caggtgcagc tggtggagtc tggaggaggc ttggcgcagc ctgggggtc tctgagactc    60
tcctgtgccg cctctggagc catcgacagt atctctgcca tgcgctggtt ccgccagcct  120
ccagggaagc agcgcgccgt ggtcgcatcg attacttccg atggtgtcac gacctacgcg  180
gactccgtga agggccgatt caccatctcc agagacaacg ccgagaacac gctgtatctg  240
caaatgaaca gcctgaaaac tgaggacacg ggcgtctatt attgttatgc agccttaaag  300
ggatattcta gtggtgtcgt cgctgcgtcc tggggacagg ggacccaggt caccgtctcc  360
ggcgcgcacc acagcgaaga cccc                                         384
```

SEQ ID NO: 3
Length: 23
Molecule Type: DNA
Features Location/Qualifiers:
source, 1 . . . 23
mol_type, other DNA
note, Primer VHH F1
organism, synthetic construct Residues:
```
gtcctggctg ctcttctaca agg                                           23
```

SEQ ID NO: 4
Length: 23
Molecule Type: DNA
Features Location/Qualifiers:
source, 1 . . . 23
mol_type, other DNA
note, Primer VHH R1
organism, synthetic construct Residues:
```
ggtacgtgct gttgaactgt tcc                                           23
```

SEQ ID NO: 5
Length: 52
Molecule Type: DNA
Features Location/Qualifiers:
source, 1 . . . 52
mol_type, other DNA
note, Primer Sfi I-VHH F2
organism, synthetic construct Residues:
```
gccatgactt ataggccc aggcggccca gttgcagctc gtggagtcag ga             52
```

SEQ ID NO: 6
Length: 57
Molecule Type: DNA
Features Location/Qualifiers:
source, 1 . . . 57
mol_type, other DNA
note, Primer Sfi I-VHH R2
organism, synthetic construct Residues:
```
gccatgactt ataggccg gcctggccgg ggtcttcgct gtggtgcgcc gaggaga        57
```

SEQ ID NO: 7
Length: 22
Molecule Type: DNA
Features Location/Qualifiers:
source, 1 . . . 22
mol_type, other DNA
note, Primer pComb3x-F
organism, synthetic construct Residues:
```
aagacagcta tcgcgattgc ag                                            22
```

SEQ ID NO: 8
Length: 24
Molecule Type: DNA
Features Location/Qualifiers:
source, 1 . . . 24
mol_type, other DNA
note, Primer pComb3x-R

Sequence Listing Information:

organism, synthetic construct

Residues:
gccccttat tagcgtttgc catc                                                  24

SEQ ID NO: 9
Length: 54
Molecule Type: DNA
Features Location/Qualifiers:
source, 1 . . . 54
mol_type, other DNA
note, Primer VHH-F
organism, synthetic construct Residues:
ggtggtgtac atctcctaca tctacgcccc cgggcaggtg cagctggtgg agtc               54

SEQ ID NO: 10
Length: 59
Molecule Type: DNA
Features Location/Qualifiers:
source, 1 . . . 59
mol_type, other DNA
note, Primer VHH-R
organism, synthetic construct Residues:
atggtgatgg tggtgctcga gttagtggtg gtggtggtgg tgagaggaga cggtgacct          59

END

---

What is claimed is:

1. A canine parvovirus (CPV) antibody CPV-VHH-H1, wherein a heavy-chain variable region sequence of the antibody has the amino acid sequence set forth in SEQ ID NO: 1.

2. A gene encoding the antibody CPV-VHH-H1 according to claim 1, comprising the nucleotide sequence set forth in SEQ ID NO: 2.

3. An expression vector comprising the gene according to claim 2.

4. An isolated host cell comprising the expression vector according to claim 3.

5. The isolated host cell according to claim 4, wherein the isolated host cell is a HEK293F cell.

6. An anti-CPV vaccine comprising the antibody CPV-VHH-H1 according to claim 1.

7. An anti-CPV composition comprising the antibody CPV-VHH-H1 according to claim 1.

* * * * *